US007189398B2

(12) United States Patent
Kaempfer et al.

(10) Patent No.: US 7,189,398 B2
(45) Date of Patent: *Mar. 13, 2007

(54) BROAD SPECTRUM PYROGENIC EXOTOXINS ANTAGONISTS AND VACCINES

(75) Inventors: Raymond Kaempfer, Jerusalem (IL); Gila Arad, Jerusalem (IL)

(73) Assignee: Yissum Research Development Company of the Hebrew University of Jerusalem, Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,947

(22) Filed: Sep. 10, 1998

(65) Prior Publication Data

US 2002/0028211 A1 Mar. 7, 2002

Related U.S. Application Data

(63) Continuation-in-part of application No. PCT/IL97/00438, filed on Dec. 30, 1997.

(51) Int. Cl.
*A61K 39/00* (2006.01)
*A61K 39/38* (2006.01)
*A61K 39/385* (2006.01)
*C07K 14/00* (2006.01)
*C07K 16/00* (2006.01)

(52) U.S. Cl. .............................. 424/184.1; 424/185.1; 424/193.1; 424/234.1; 424/235.1; 424/236.1; 424/237.1; 424/244.1; 435/243; 435/253.4; 530/300; 530/350

(58) Field of Classification Search ............... 530/350, 530/820, 825, 300; 435/243, 253.4; 424/184.1, 424/185.1, 193.1, 234.1, 236.1, 237.1, 235.1, 424/244.1
See application file for complete search history.

(56) References Cited

U.S. PATENT DOCUMENTS

| 5,310,874 A | * | 5/1994 | Tamura et al. ............... 530/324 |
| 5,407,609 A | * | 4/1995 | Tice et al. | |
| 5,545,716 A | | 8/1996 | Johnson et al. | |
| 5,705,151 A | * | 1/1998 | Dow et al. | |

FOREIGN PATENT DOCUMENTS

| EP | 499 681 | * | 8/1992 |
| JP | 61178661 A1 | | 8/1986 |
| WO | 9110680 A1 | | 7/1991 |
| WO | 9112818 A1 | | 9/1991 |
| WO | 9640235 A1 | | 12/1996 |

OTHER PUBLICATIONS

Huang et al. J Biol Chem 245(14) : 3518-3525, 1970.*
Galinsei et al (Virology vol. 155 pp. 46-60), 1986.*
Spriggs et al (J. Gen. Virol. vol. 67, pp. 2705-2719), 1986.*
Schlievert P. M., Role of superantigens in human disease (1993) *J Infect Dis* 167:997.
Marrack P. and Kappler J., The staphylococcal enterotoxins and their relatives (1990) *Science* 248:705.
Tseng J. et al., Humoral immunity to aerosolized staphylococcal enterotoxin B (SEB), and superantigen, in monkeys vaccinated with SEB toxoid-containing microspheres (1995) *Infect Immun* 63:2880.
Murray D. L. et al., Staphylococcal and Streptococcal superantigens: their role in human diseases (1995) *ASM News* 61:229.
Bohach G. A. et al., Staphylococcal and Streptococcal pyrogenic toxins involved in toxic shock syndrome and related illnesses (1990) *Crit Rev Microbiol* 17:251.
Lowell G. H. et al., Intranasal and intramuscular proteosome0staphylococcal enterotoxin B (SEB) toxoid vaccines: immunogenicity and efficacy against lethal SEB intoxication in mice (1996) *Infect Immun* 64:1706.
Hoffman M., "Superantigens" may shed light on immune puzzle (1990) *Science* 248:685.
Smith B. G. and Johnson H. M. The effect of Staphylococcal enterotoxins on the primary *in vitro* immune response (1975) *J Immunol* 115:575.
Marrack P. et al., The toxicity of staphylococcal enterotoxin B in mice is mediated by T cells (1990) *J Exp Med* 171:455.
Pinto M. et al., Suppression of the in vivo humoral and cellular immune response by staphylococcal enterotoxin B (SEB) (1978) *Transplantation* 25:320.
Ketzinel M. et al., Regulation of human interleukin-2 and interferon-gamma gene expression by suppressor T lymphocytes (1991) *Scand J Immunol* 33:593.

(Continued)

*Primary Examiner*—Mark Navarro
(74) *Attorney, Agent, or Firm*—Browdy and Neimark, PLLC

(57) ABSTRACT

The invention relates to peptides having an amino acid sequence substantially homologous to an amino sequence of a domain of a pyrogenic exotoxin, which domain forms a central turn in the exotoxin starting within β-strand 7 and connecting the β-strand 7, via short β-strand 8, to α-helix 4, and ending within α-helix 4, based on the domain numbering of *Staphylococus aureus* enterotoxin B. The peptides of the invention are capable of antagonizing toxin-mediated activation of T-lymphocytes, do not have agonist activity, and are capable of eliciting protective immunity against toxic shock induced by a pyrogenic exotoxin or by a mixture of pyrogenic exotoxins. The invention also relates to broad spectrum pharmaceutical compositions for the treatment, protection against or short term prophylaxis of toxin-mediated activation of T cells, comprising as active ingredient at least one peptide according to the invention or a derivative thereof, and to broad spectrum vaccines for conferring long term immunity against toxic shock induced by at least one pyrogenic exotoxin.

48 Claims, 18 Drawing Sheets

OTHER PUBLICATIONS

Figure 2:
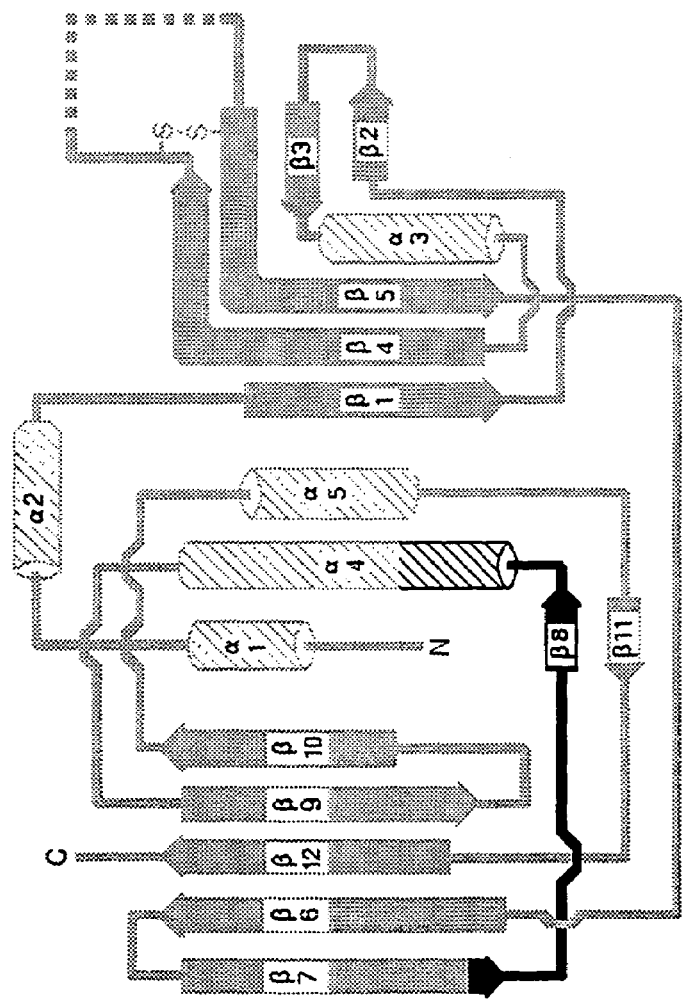

Arad G. et al., Transient expression of human interleukin-2 and interferon-γ genes is regulated by interaction between distinct cell subsets (1995) *Cell Immunol* 160:240.

Mosmann T. R. and Coffman R. L., TH1 and TH2 cells (1989) *Ann Rev Immunol* 7:145.

Herman A. et al., Superantigens: mechanism of T-cell stimulation and role in immune responses (1991) *Ann Rev Immunol* 9:745.

Janeway C. A. et al., T-Cell responses to mls and to bacterial proteins that mimic its behavior (1989) *Immunol Rev* 107:61.

Choi Y. et al., Residues of variable region of the T-cell-receptor β-chain that interact with S. *aureus* toxin superantigens (1990) *Nature* 346:471.

Choi Y. et al., Interaction of *Staphylococcus aureus* toxin "superantigens" with human T cells (1989) *Proc Natl Acad Sci U.S.A.* 86:8941.

Scholl P. et al., Toxic shock syndrome toxin I binds to major histocompatibility complex class II molecules (1989) *Proc Natl Acad Sci U.S.A.* 86:4210.

Fleischer B. and Schrezenmeier H. T-Cell stimulation by staphylococcal enterotoxins (1988) *J Exp Med* 167:1697.

Fraser J. D. High-affinity binding of staphylococcal enterotoxins A and B to HLA-DR (1989) *Nature* 339:221.

Misfeldt M. L. Microbial "Superantigens" (1990) *Infect Immun* 58:2409.

Janeway C. A. Self superantigens? (1990) *Cell* 63:659.

Schad E. M. et al., Crystal structure of the superantigen staphylococcal enterotoxin type A (1995) *EMBO J* 14:3292.

Ikejima T. et al., Induction of human interleukin-1 by a product of *Staphylococcus aureus* associated with toxic shock syndrome (1984) *J Clin Invest* 73:1312.

Poindexter N. J. and Schlievert P. M., Suppression of immunoglobulin-secreting cells from human peripheral blood by toxic-shock-syndrome Toxin-1 (1986) *J Infect Dis* 153:772.

Uchiyama T. et al., Activation of murine T cells by toxic shock syndrome toxin-1 (1989) *J Immunol* 143:3173.

Jett M. et al., Identification of Staphylococcal enterotoxin B sequences important for induction of lymphocyte proliferation by using synthetic peptide fragments of the toxin (1994) *Infect Immun* 62:3408.

Mayordomo J. et al., Therapy of murine tumors with p53 wild-type and mutant sequence peptide-based vaccines (1996) *J Exp Med* 183:1357.

Hughes E. E. and Gilleland H. E. Ability of synthetic peptides representing epitops of outer membrane protein F of *Pseudomonas aeruginosa* to afford protection against *P. aeruginosa* infection in a murine acute pneumonia model (1995) *Vaccine* 13:1750.

Brander C. et al. Peptide immunization in humans (1996) *Clin Exp Immunol* 105:18.

Swaminathan S. et al., Crystal structure of Staphylococcal enterotoxin B, a superantigen (1992) *Nature* 359:801.

Bohach G. A. and Schlievert P. M., Nucleotide sequence of the staphylococcal enterotoxin C1 gene and relatedness to other pyrogenic toxins (1987) *Mol Genet* 209:5.

Couch J. L. et al., Cloning and nucleotide sequence of the type E staphylococcal enterotoxin gene (1988) *J Bacteriol* 170:2954.

Bohach G. A. and Schlievert P. M., Conservation of the biologically active portions of staphylococcal enterotoxins C1 and C2 (1989) *Infect Immun* 57:2249.

Wang B. et al., Localization of an immunologically functional region of the streptococcal superantigen pepsin-extracted fragment of type 5 M protein (1993) *J Immunol* 151:1419.

Hoffmann M. L. et al., Predictions of T-cell receptor and major histocompatibility complex binding sites on Staphylococcal enterotoxin C1 (1994) *Infect Immun* 62:3396.

Chomczynski P. and Sacchi N., Single-step method of RNA isolation by acid guanidinium thiocyanate-phenol-chloroform extraction (1987) *Anal Biochem* 162:156.

Gerez L. et al., Averrant regulation of interleukin-2 but not of interferon-γ gene expression in Down syndrome (1991) *Clin Immunol Immunopathol* 58:251.

Kaempfer R. et al., Prediction of response to treatment in superficial bladder carcinoma through pattern of interleukin-2 gene expression (1996) *J Clin Oncol* 14:1778.

Mallett C. P. et al., Intranasal or intragastric immunization with proteosome-Shigella lipopolysaccharide vaccines protects against lethal pneumoia in murine model (1995) *Infect Immun* 63:2382.

Jardetzky T. S. et al., Three dimensional structure of a human class II histocompatibility molecule complexed with superantigen (1994) *Nature* 368:711.

Betley M. J. and Mekalanos J. J., Nucleotide sequence of the type A staphylococcal enterotoxin gene (1995) *J Bacteriol* 170:34.

Komisar J. L. et al., Localization of binding sites of staphylococcal enterotoxin B (SEB), a superantigen, for HLA-DR by inhibition with synthetic peptides of SEB (1994) *Infect Immun* 62:4775.

Buelow et al., Localization of the immunologic activity in the superantigen staphylococcal enterotoxin B using truncated recombinant fusion proteins (1992) *J Immunol* 148:1.

Kappler J. W. et al., Mutations defining functional regions of the superantigen staphylococcal enterotoxin B (1992) *J Exp Med* 175:387.

Lowell G. H. et al., Immunogenicity and efficacy against lethal aerosol staphylococcal enterotoxin B challenge in monkeys by intramuscular and respiratory delivery of proteosome-toxoid vaccines (1996b) *Infect Immun* 64:4686.

Stiles B. G. et al., Biological activity of toxin shock syndrome toxin 1 and a site-directed mutant, H135A, in a lipopolysaccharide-potentiated mouse lethality model (1995) *Infect. Immun.* 63:1229.

Woody M. A. et al., Staphylococcal enterotoxin B mutants (N23K and F44S): biological effects and vaccine potential in a mouse model (1997) *Vaccine* 15:133.

Sakita I. et al., In vivo CTL immunity can be elicited by in vitro reconstituted MHC/peptide complex (1996) *J. Immunol. Methods* 192:105.

Kuchroo V. K. et al., A single TCR antagonist peptide inhibits experimental allergic encephalomyelitis mediated by a diverse T cell repertoire (1994) *J. Immunol.* 153:3326.

Williams W. V. et al., Modulation of T cell responses with MHC-derived peptides (1992) *Immunol Res* 11:11.

Seelig G. F. et al., Development of a receptor peptide antagonist to human γ-interferon and characterization of its ligand-bound conformation using transferred nuclear overhauser effect spectroscopy (1995) *J Biol Chem* 270:9241.

Williams W. V. et al., Design of bioactive peptides based on antibody hypervariable region structures (1991) *J Biol Chem* 266:5182.

Cardarelli P. M. et al., The collagen receptor α2β1, from MG-63 and HT1080 cells, interacts with a cyclic RGD peptide (1992) *J Biol Chem* 267:23159.

Dyer C. A. and Curtiss L. K., A synthetic peptide mimic of plasma apolipoprotein E that binds the LDL receptor (1991) *J Biol Chem* 266:22803.

Reitman B. H. et al., Protected peptide disulfides by oxidative detachment from a support (1994) *Int J Pept Protein Res* 44:199.

Toniolo C., Conformationally restricted peptides through short-range cyclizations (1990) *Int J Peptide Protein Res* 35:287.

Gilon C. et al., Backbone cyclization: a new method for conferring conformational constraint on peptides (1991) *Biopolymers* 31:745.

Lowell G et al., "Mucosal Immunogenicity and efficacy of Proteosomes and PA Adjuvantsfor HIV Influenza, Shigella & Staph. Entrotoxin B (SEB) Vaccines", Journal of Cellular Biochemistry, Jan. 5, 1995, pp. 259, vol. 19A, Abstract J1-220.

\* cited by examiner

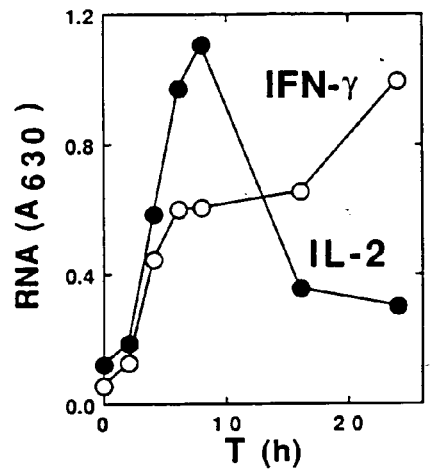
Figure 1A
Figure 1B
Figure 1C
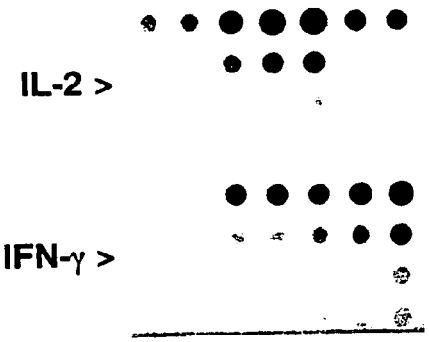
Figure 1D
Figure 1E

Figure 10A / Figure 10B / Figure 10C / Figrue 10D

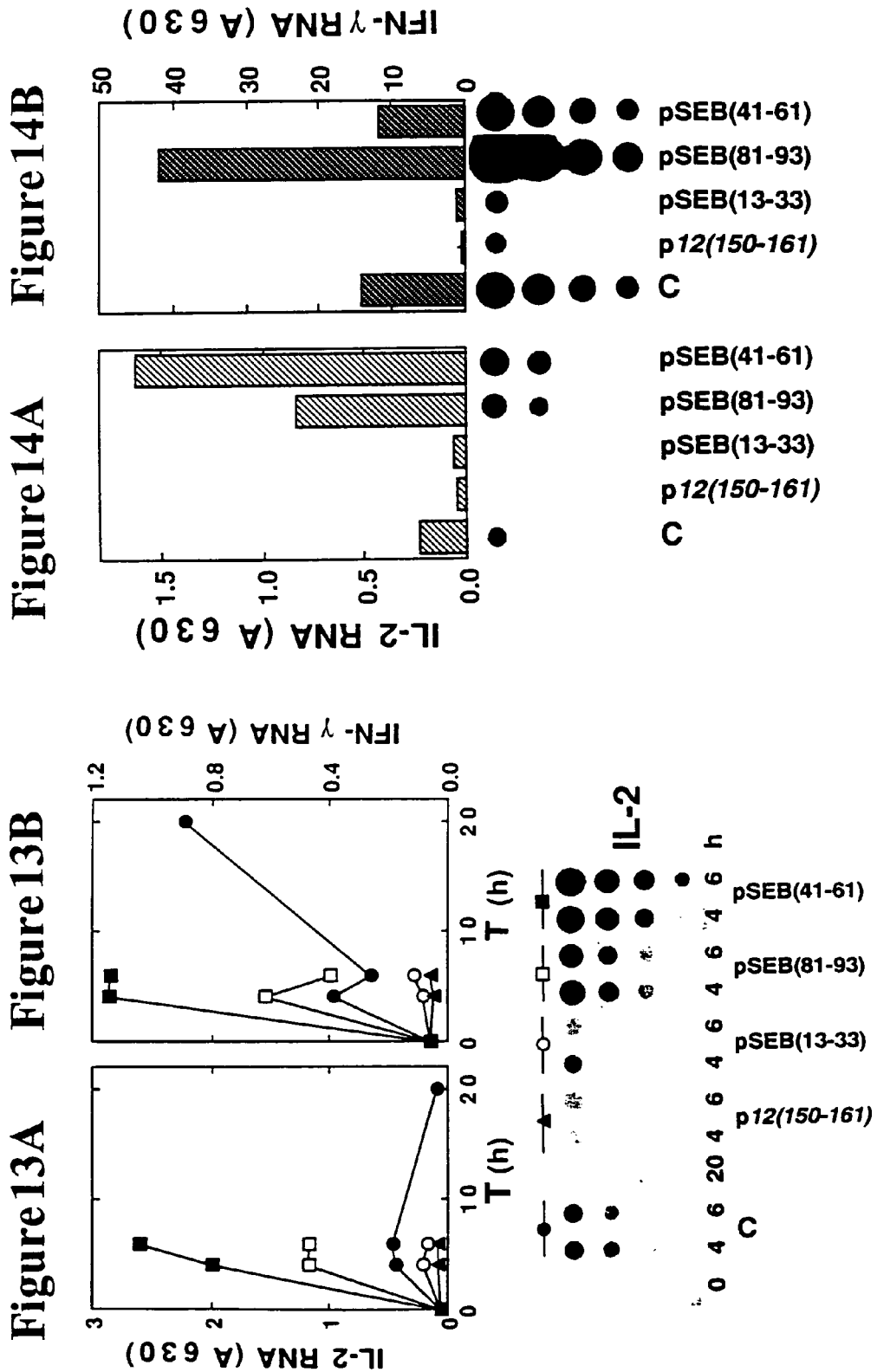

Protection Against SEB

Figure 16

Protection by a Low Dose of p12

SEQUENCE LISTING

<160> NUMBER OF SEQ ID NOS: 12

<210> SEQ ID NO 1
<211> LENGTH: 26
<212> TYPE: PRT
<213> ORGANISM: Staphylococcus aureus

<400> SEQUENCE: 1

Ser Glu Gln Glu Asn Cys Glu Leu Ile Ser Thr Ile Asn Gly Thr Asn
1               5                   10                  15

Lys Lys Lys Val Thr Ala Gln Glu Leu Asp
            20                  25

<210> SEQ ID NO 2
<211> LENGTH: 12
<212> TYPE: PRT
<213> ORGANISM: Staphylococcus aureus

<400> SEQUENCE: 2

-continued

Tyr Asn Lys Lys Lys Ala Thr Val Gln Glu Leu Asp
1               5                   10

<210> SEQ ID NO 3
<211> LENGTH: 10
<212> TYPE: PRT
<213> ORGANISM: Staphylococcus aureus

<400> SEQUENCE: 3

Lys Lys Lys Val Thr Ala Gln Glu Leu Asp
1               5                   10

<210> SEQ ID NO 4
<211> LENGTH: 10
<212> TYPE: PRT
<213> ORGANISM: Staphylococcus aureus

<400> SEQUENCE: 4

Lys Lys Lys Ala Thr Val Gln Glu Leu Asp
1               5                   10

<210> SEQ ID NO 5
<211> LENGTH: 13
<212> TYPE: PRT
<213> ORGANISM: Staphylococcus aureus
<220> FEATURE:
<221> NAME/KEY: LIPID
<222> LOCATION: (1)...(1)
<223> OTHER INFORMATION: N-lauryl cysteine residue

<400> SEQUENCE: 5

Cys Thr Asn Lys Lys Lys Val Thr Ala Gln Glu Leu Asp
1               5                   10

<210> SEQ ID NO 6
<211> LENGTH: 13
<212> TYPE: PRT
<213> ORGANISM: Staphylococcus aureus
<220> FEATURE:
<221> NAME/KEY: LIPID
<222> LOCATION: (1)...(1)
<223> OTHER INFORMATION: N-lauryl cysteine residue

<400> SEQUENCE: 6

Cys Tyr Asn Lys Lys Lys Ala Thr Val Gln Glu Leu Asp
1               5                   10

<210> SEQ ID NO 7
<211> LENGTH: 16
<212> TYPE: PRT
<213> ORGANISM: Staphylococcus aureus

<400> SEQUENCE: 7

Tyr Asn Lys Lys Lys Ala Thr Val Gln Glu Leu Asp Tyr Asn Lys Lys
1               5                   10                  15

<210> SEQ ID NO 8
<211> LENGTH: 35
<212> TYPE: PRT
<213> ORGANISM: Staphylococcus aureus

<400> SEQUENCE: 8

Tyr Asn Lys Lys Lys Ala Thr Val Gln Glu Leu Asp Tyr Asn Lys Lys
1               5                   10                  15

Lys Ala Thr Val Gln Glu Leu Asp Tyr Asn Lys Lys Lys Ala Thr Val
            20                  25                  30

```
Glu Leu Asp
        35

<210> SEQ ID NO 9
<211> LENGTH: 14
<212> TYPE: PRT
<213> ORGANISM: Staphylococcus aureus
<220> FEATURE:
<221> NAME/KEY: DISULFID
<222> LOCATION: (1)...(1)
<221> NAME/KEY: DISULFID
<222> LOCATION: (14)...(14)

<400> SEQUENCE: 9

Cys Tyr Asn Lys Lys Lys Ala Thr Val Gln Glu Leu Asp Cys
 1               5                  10

<210> SEQ ID NO 10
<211> LENGTH: 14
<212> TYPE: PRT
<213> ORGANISM: Staphylococcus aureus
<220> FEATURE:
<221> NAME/KEY: MOD_RES
<222> LOCATION: (1)...(1)
<223> OTHER INFORMATION: D-alanine
<221> NAME/KEY: MOD_RES
<222> LOCATION: (14)...(14)
<223> OTHER INFORMATION: D-alanine

<400> SEQUENCE: 10

Xaa Tyr Asn Lys Lys Lys Ala Thr Val Gln Glu Leu Asp Xaa
 1               5                  10

<210> SEQ ID NO 11
<211> LENGTH: 13
<212> TYPE: PRT
<213> ORGANISM: Staphylococcus aureus
<220> FEATURE:
<221> NAME/KEY: ACETYLATION
<222> LOCATION: (1)...(1)
<223> OTHER INFORMATION: N-acetyl group
<221> NAME/KEY: MOD_RES
<222> LOCATION: (13)...(13)
<223> OTHER INFORMATION: D-alanine

<400> SEQUENCE: 11

Tyr Asn Lys Lys Lys Ala Thr Val Gln Glu Leu Asp Xaa
 1               5                  10

<210> SEQ ID NO 12
<211> LENGTH: 239
<212> TYPE: PRT
<213> ORGANISM: Staphylococcus aureus

<400> SEQUENCE: 12

Glu Ser Gln Pro Asp Pro Lys Pro Asp Glu Leu His Lys Ser Ser Lys
 1               5                  10                  15

Phe Thr Gly Leu Met Glu Asn Met Lys Val Leu Tyr Asp Asp Asn His
            20                  25                  30

Val Ser Ala Ile Asn Val Lys Ser Ile Asp Gln Phe Leu Tyr Phe Asp
        35                  40                  45

Leu Ile Tyr Ser Ile Lys Asp Thr Lys Leu Gly Asn Tyr Asp Asn Val
    50                  55                  60

Arg Val Glu Phe Lys Asn Lys Asp Leu Ala Asp Lys Tyr Lys Asp Lys
65                  70                  75                  80
```

-continued

```
Tyr Val Asp Val Phe Gly Ala Asn Tyr Tyr Gln Cys Tyr Phe Ser
            85                  90              95

Lys Lys Thr Asn Asp Ile Asn Ser His Glu Thr Asp Lys Arg Lys Thr
            100             105             110

Cys Met Tyr Gly Gly Val Thr Glu His Asn Gly Asn Gln Leu Asp Lys
        115             120             125

Tyr Arg Ser Ile Thr Val Arg Val Phe Glu Asp Gly Lys Asn Leu Leu
    130             135             140

Ser Phe Asp Val Gln Thr Asn Lys Lys Val Thr Ala Gln Glu Leu
145             150             155             160

Asp Tyr Leu Thr Arg His Tyr Leu Val Lys Asn Lys Lys Leu Tyr Glu
            165             170             175

Phe Asn Asn Ser Pro Tyr Glu Thr Gly Tyr Ile Lys Phe Ile Glu Asn
            180             185             190

Glu Asn Ser Phe Trp Tyr Asp Met Met Pro Ala Pro Gly Asp Lys Phe
        195             200             205

Asp Gln Ser Lys Tyr Leu Met Met Tyr Asn Asp Asn Lys Met Val Asp
    210             215             220

Ser Lys Asp Val Lys Ile Glu Val Tyr Leu Thr Thr Lys Lys Lys
225             230             235
```

BROAD SPECTRUM PYROGENIC EXOTOXINS ANTAGONISTS AND VACCINES

CROSS-REFERENCE TO RELATED APPLICATIONS

This is a continuation-in-part application of International Patent Application PCT/IL97/00438, filed Dec. 30, 1997, which claims priority to Israeli Patent Application No. 119938, filed Dec. 30, 1996.

The U.S. Government has a nonexclusive, nontransferable, irrevocable paid-up license to practice or have practiced this invention for or on its behalf as provided for by the terms of Contract No. DAMD17-93-C-3108 awarded by the U.S. Department of the Army.

FIELD OF THE INVENTION

The invention relates to peptides structurally related to protein domains in pyrogenic exotoxins, capable of antagonizing activation of T cells mediated by said exotoxins and of eliciting protective immunity against toxic shock induced by said exotoxins. The invention further relates to pharmaceutical preparations containing the said peptides, for the treatment or prophylaxis of toxic shock and to vaccines containing the said peptides, capable of eliciting protective immunity against toxic shock induced by said exotoxins.

BACKGROUND OF THE INVENTION

A family of pyrogenic exotoxins, also known as superantigenic toxins, is produced by *Staphylococcus aureus* and *Streptococcus pyogenes*. The exotoxins comprised of the *S. aureus* enterotoxins (SEs) cause the majority of human food poisoning cases manifested by vomiting and diarrhea after ingestion [Schlievert, J Infect Dis 167:997 (1993)]. *S. aureus* is found widespread in nature, often in association with humans. Among the 5 major serological types within the family of SEs (labeled SEA to SEE and SEG), SEB is the most prominent [Marrack and Kappler, Science 248:705 (1990)]. SEB has also been recognized as a leading cause of human cases of non-menstrual toxic shock syndrome that can accompany surgical or injurious wound infections, as well as viral infections of the respiratory tract of influenza patients to which children are especially vulnerable [Schlievert (1993) ibid.; Tseng et al., Infect Immun 63:2880 (1995)]. Toxic shock syndrome, in its most severe form, causes shock and death [Murray et al., ASM News 61:229 (1995); Schlievert (1993) ibid.]. More generally, members of the staphylococcal exotoxin family, including SEA to SEE and toxic shock syndrome toxin 1 (TSST-1), have been implicated in toxic shock syndrome, in atopic dermatitis [Schlievert (1993) ibid.] and in Kawasaki's syndrome [Bohach et al., Crit Rev Microbiol 17:251 (1990)].

Because of the potential for causing lethal shock in humans after aerosol exposure and because of the relative ease with which SEB can be produced in large amounts, there is concern that SEB could be used as a biological weapon [Lowell et al., Infect Immun 64:1706 (1996)]. SEB is thought to be a biological weapon mainly in view of its lethal potential. However, through its exquisite ability to induce vomiting and diarrhea, SEB is also an incapacitating agent that could severely impair the effectiveness of a fighting force, even temporarily, thereby enhancing vulnerability to conventional military means. Needless to say, the harmful effects of SEB need to be generally attacked, and not only in connection with the military aspect.

SEB is a toxic mitogen that triggers a paradoxical response in the infected organism: a vast stimulation of the immune system on one hand side and, on the other hand, a profound immunosuppression that may allow the multiplication of the infecting bacteria, unimpeded by an immune response [Hoffman, Science 248:685 (1990); Smith and Johnson J Immunol 115:575 (1975); Marrack et al, J Exp Med 171:455 (1990); Pinto et al., Transplantation 25:320 (1978)]. During the cellular immune response, a dynamic interplay is induced, by antigens or mitogens, between activation of Th1 type cytokine gene expression on one hand, exemplified by interleukin-2 (IL-2), interferon-γ (IFN-γ) and tumor necrosis factor-β (TNF-β), and on the other hand, its cell-mediated suppression by CD8 cells and other cell subsets [Ketzinel et al., Scand J Immunol 33:593 (1991); Arad et al., Cell Immunol 160:240 (1995)], and by the inhibitory cytokines from Th2 cells, IL-4 and IL-10 [Mosmann and Coffman, Annu Rev Immunol 7:145 (1989)].

SEB is a member of the family of pyrogenic exotoxins [Herman et al., Ann Rev Immunol 9:745 (1991)] that comprises bacterial exotoxins and Mls proteins. These agents stimulate a 20,000-fold greater proportion of rodent or human T cells than do ordinary antigens. Thus, SEB activates 30–40% of all T cells in some mice to divide and produce cytokines [Marrack and Kappler (1990) ibid.]. Indeed, expression of the toxicity of SEB requires T cells; mice that lack T cells or SEB-reactive T cells are not affected by doses of SEB that cause weight loss and death in normal animals [Marrack et al. (1990) ibid.; Marrack and Kappler (1990) ibid.]. Unlike normal antigens, SEB and related toxic mitogens do not require processing and antigen presentation [Janeway et al., Immunol Rev 107:61 (1989)] but activate the T cell by binding at a specific site in the variable portion of the β chain (V-β) of the T-cell receptor [Choi et al., Nature 346:471 (1990)]. The crucial region for T-cell receptor interaction with toxin lies on the outer face of the V-β domain, a region not involved in conventional antigen recognition [Choi et al., Proc Natl Acad Sci U.S.A. 86:8941 (1989)]. Simultaneously, pyrogenic exotoxins bind directly to MHC class II molecules [Scholl et al., Proc Natl Acad Sci U.S.A. 86:4210 (1989)] and thus affect primarily $CD4^+$ T cells, although $CD8^+$ cells are also activated [Fleischer and Schrezenmeier, J Exp Med 167:1697 (1988); Fraser, Nature 339:221 (1989); Misfeldt, Infect Immun 58:2409 (1990)]. The current consensus is that pyrogenic exotoxins activate T cells so effectively because they bypass the ordinary interaction of antigen with class II MHC and T-cell receptor [Janeway, Cell 63:659 (1990)]. An alternative view is that pyrogenic exotoxins act as coligands that facilitate and thus greatly exaggerate the effect of minute amounts of ordinary antigens [Janeway (1990) ibid.].

The toxicity of SEB and related exotoxins is thought to be related to the capacity of these molecules to stimulate the rapid and excessive production of cytokines, especially of IL-2, IFN-γ and tumor necrosis factors (TNFs). IL-2, IFN-γ, and TNF-β are secreted from activated T helper type 1 (Th1cells while TNF-α is secreted by Th1 cells, monocytes and macrophages. High levels of these cytokines, suddenly produced, have been implicated as a central pathogenic factor in toxin-related toxicity [Schad et al., EMBO J 14:3292 (1995)] and are thought to cause a rapid drop in blood pressure leading to toxic shock.

While investigation has produced a plausible explanation for the vast stimulation of T cells by SEs, it is not yet clear why these toxins are also strongly immunosuppressive. They induce a decline in both primary T and B cell responses, including the production of antibodies and the generation of plaque-forming cells [Hoffman (1990) ibid.; Smith and Johnson (1975) ibid.; Marrack et al. (1990) ibid.; Pinto et al., (1978) ibid.; Ikejima et al., J Clin Invest 73:1312 (1984); Poindexter and Schlievert, J Infect Dis 153:772 (1986)].

The sensitivity of humans to staphylococcal toxins exceeds that of mice by a factor of 100. Thus, the toxic shock syndrome toxin 1, TSST-1, another pyrogenic exotoxin from *Staphylococcus aureus*, stimulates human T cells to express the key is cytokines, IL-2, IFN-γ and TNF-β at <0.1 pg/ml, while murine cells require approximately 10 pg/ml [Uchiyama et al., J Immunol 143:3173 (1989)]. Mice may have developed relative resistance to toxic mitogens by deleting from their T cell repertoire those cells that display the most highly reactive V-β chains or by eliminating these V-β genes [Marrack and Kappler (1990) ibid.]. Such deletions have not been detected in humans, making them far more vulnerable.

The incapacitating and potentially lethal effects for humans of SEB (and of exotoxins of the same family of superantigens), whether exerted on civilians or military personnel, create a need for prophylaxis against SEB, for treatment of SEB-exposed individuals and for a safe SEB vaccine.

Despite the urgency of this need, methods of protection or treatment have been lacking. Thus, in D-galactosamine-sensitized murine models of SEB intoxication, one based on intramuscular challenge with SEB toxin and the other on intranasal challenge using mucosal SEB exposure, it was possible to protect mice with proteosome-SEB toxoid vaccines in which the SEB toxoid component was prepared by a 30-day formalin treatment of the biologically active, intact SEB protein molecule [Lowell et al. (1996) ibid.]. As detailed below, however, the inventors have now found that antibodies raised against certain peptide domains within the SEB molecule enhance the ability of SEB to stimulate human T cells, rather than protecting them against the toxin. This finding limits the use of SEB toxoids as vaccine, in view of the danger of eliciting certain SEB-sensitizing antibodies that could not only fail to confer protective immunity but would lead to significant exacerbation of the toxic responses in SEB-exposed persons.

Other investigators sought recourse in the use of fragments rather than the complete SEB protein molecule, through the synthesis of a series of overlapping SEB peptides, in the order of 30 amino acids each in length [Jett et al., Infect Immun 62:3408 (1994)]. These peptides were used to generate antisera in rabbits whose ability to inhibit the SEB-induced proliferation of a mixture of human T cells and macrophages was then tested. That effort failed to yield an effective or specific inhibitory response. Thus, peptide pSEB(113–144), containing amino acids 113 to 144 of the SEB protein molecule, as well as peptides covering amino acids 130–160, 151–180, and 171–200 each elicited antisera that inhibited the SEB-induced lymphocyte proliferation weakly, by up to 2.5-fold [Jett et al. (1994) ibid.].

A number of investigators attempted the create peptide vaccines. Thus, Mayordomo et al. [J Exp Med 183:1357 (1996)] used a mutant peptide derived from p53 as vaccine for therapy of murine tumors. Hughes and Gilleland [Vaccine 13:1750 (1995)] used synthetic peptides representing epitopes of outer membrane protein F of *Pseudomonas aeruginosa* to afford protection against *P. aeruginosa* infection in a murine acute pneumonia model. In an attempt to use peptide immunization in humans Brander et al. [Clin Exp Immunol 105:18 (1996)] showed that a combined CD8+/CD4+ T cell-targeted vaccine restimulated the memory CD4+ T cell response but failed to induce cytotoxic T lymphocytes.

Major sources of exotoxins are, as already mentioned, *S. Aureus* and *S. Pyogenes*. The flesh-eating bacteria, *S. Pyogenes*, produce a family of different toxins with closely similar mode of action: excessive activation of T cells. *S. Aureus* produces next to SEB as major component, also SEA, SECs, SEE and TSST-1 (toxic shock syndrome toxin 1) and *S. Pyogenes* produces SPE A as major toxin, as well as other pyrogenic exotoxins. Hence, in staphylococcal food poisonings and, more seriously, in biological warfare or in toxic shock caused by *S. pyogenes*, mixtures of toxins are encountered. The composition of such mixtures cannot be anticipated with certainty. The worst scenarios of biological warfare entail not the use of a single, purified pyrogenic exotoxin, as favored for immunological studies, but rather a readily attainable, crude natural mixtures of such toxins, as produced, for example, by culturing *S. Aureus*.

Clearly, this complexity demands the development of broad-spectrum antagonists of pyrogenic exotoxins as well as broad-spectrum vaccines.

There exists, therefore, a long-felt need to design a SEB vaccine that is free of sensitizing potential, yet is capable of protecting test animals or humans against lethal doses of the toxin. Even greater value would be inherent in a vaccine that can afford protection not only against SEB, but also against a wider spectrum of the SE toxin family, including, for example, SEA.

Moreover, currently, there is no prophylaxis available against SEB or any other pyrogenic exotoxin, nor treatment of exposed persons. There exists, therefore, also a long-felt need to design agents that antagonize the action of SEB, as well as any other pyrogenic exotoxin. Such antidotes will have great value, both in the medical treatment of acute food poisoning and in saving lives in cases of toxic shock and related pathological conditions.

There exists therefore a need, on the one hand, for an antagonist against pyrogenic exotoxins, for use in immediate treatment, or short term prevention and rapid prophylaxis, of acute toxic shock and of the harmful effects of such toxins which may be due to, for example, accidental food poisoning, and on the other hand, for a vaccine for immunization against intoxication by pyrogenic exotoxins, for long term protection thereagainst.

In addition, currently there is no way by which to assess the efficacy of vaccination of humans against pyrogenic toxins, since humans cannot be challenged with the toxin in order to check whether they have been conferred the desired immunity. There exists therefore a need for a clinical test for assessing the efficacy of vaccination of humans against pyrogenic toxins which employs surrogate markers.

SUMMARY OF THE INVENTION

The present invention relates to peptides comprising an amino acid sequence substantially homologous to the amino acid sequence of a fragment of a pyrogenic exotoxin, and derivatives of said peptides, capable of eliciting protective immunity against toxic shock induced by a pyrogenic exotoxin or by a mixture of pyrogenic exotoxins.

The present invention also relates to peptides comprising an amino acid sequence substantially homologous to the amino acid sequence of a fragment of a pyrogenic exotoxin, and derivatives of said peptides, capable of antagonizing toxin-mediated activation of T cells.

Also within the scope of this invention are peptide comprising an amino acid sequence substantially homologous to the amino acid sequence of a fragment of a pyrogenic exotoxin, and derivatives thereof, which are capable of protecting against toxic shock induced by a pyrogenic exotoxin or by a mixture of pyrogenic exotoxins.

The peptides of the invention comprise an amino acid sequence substantially homologous to the amino sequence of a fragment of *Staphylococcal aureus* enterotoxin B (SEB).

The pyrogenic exotoxin is a bacterial exotoxin produced by *Staphylococcus aureus* or *Streptococcus pyogenes*.

According to the invention, the peptides may be further linked through its N-terminus to a lauryl-cysteine (LC) residue and/or through its C-terminus to a cysteine (C) residue, or to other residue/s suitable for linking said peptide to adjuvant/s for immunization.

Further, the peptides may be in the form of a dimer, a multimer or in a constrained conformation, in which the constrained conformation is obtained by internal bridges, short-range cyclizations, extension or other chemical modification.

The peptides of the invention are capable of inhibiting expression of pyrogenic toxin-induced mRNA encoded by the IL-2, IFN-γ or TNF-β genes.

In addition, the peptides of the invention are capable of eliciting, in the presence of a suitable immunization adjuvant, in immunized individuals, the production of antibodies that block T-cell pyrogenic toxin-mediated activation.

In a second aspect of the invention a pharmaceutical composition is provided, for the treatment or short term prophylaxis of toxin-mediated activation of T cells, comprising as active ingredient a therapeutically effective amount of at least one peptide according to the invention or derivative thereof. The peptides of the invention are capable of protecting against toxic shock induced by a pyrogenic exotoxin or by a mixture of pyrogenic exotoxins.

Additionally, the invention provides a vaccine for conferring long term immunity against toxic shock induced by at least one pyrogenic exotoxin, comprising as active ingredient an immunologically effective amount of at least one peptide according to the invention, or derivative thereof.

Also provided by the invention is a method for the immediate treatment or short term prevention of acute toxic shock and of the harmful effects which may be due to, for example, accidental food poisoning induced by at least one pyrogenic exotoxin, comprising administering to a patient in need of such treatment a therapeutically effective amount of the pharmaceutical composition of the invention or of a therapeutically effective amount of at least one peptide of the invention.

Additionally, the invention provides a method for conferring long term immunity to toxic shock induced by a pyrogenic exotoxin or a mixture of pyrogenic exotoxins, comprising administering to a patient an effective immunizing amount of a vaccine of the invention.

In addition, the invention relates to antibodies directed against a peptide according to the invention which are capable of blocking T-cell activation by a pyrogenic exotoxin or a mixture of pyrogenic exotoxins, which may be mono- or polyclonal antibodies.

In yet a further aspect, the invention relates to an antiserum containing antibodies directed against at least one peptide of the invention, which peptide can elicit the production of the antibodies. The antiserum is capable of alleviating toxic shock induced by a pyrogenic exotoxin.

In addition, the invention provides for a method for assessing the efficacy of a vaccine for conferring immunity against one or more pyrogenic toxins comprising determining the ability of serum from an immunized individual to antagonize toxin-mediated activation of T cells. A kit for assessing the efficacy of a vaccine for conferring immunity against one or more pyrogenic toxins comprising determining the ability of serum from an immunized individual to antagonize toxin-mediated activation of T cells by the method of the invention is also provided.

DESCRIPTION OF THE FIGURES

FIGS. 1A–1E Induction of IL-2, IFN-γ and TNF-β Gene Expression by SEB Aliquots of $4\times10^6$ human PBMC were induced with SEB. Total RNA was extracted at times indicated [T(h)] and serial twofold dilutions (vertical rows) were subjected to dot blot hybridization analysis with $^{32}$P-labeled IL-2 and IFN-γ anti-sense RNA probes; autoradiograms (FIGS. 1B, 1C) were quantitated by densitometry at 630 nm, plotted in (FIG. 1A). In separate experiments, aliquots of $3\times10^7$ human PBMC were induced with SEB and total RNA was extracted at times indicated. IL-2, IFN-γ (FIG. 1D) and TNF-β mRNA (FIG. 1E) was quantitated by RNase protection analysis. IL-2 mRNA protects a fragment of 117 nt; IFN-γ mRNA protects a fragment of 183 nt; TNF-β mRNA protects 2 fragments of 274 and 263 nt. β-Actin RNA served as loading control.

FIG. 2 Secondary structure domains within the SEB protein molecule The two structural domains of the molecule are seen clearly. Cylinders and arrows represent α-helices and β-strands, respectively. The residues forming the secondary structural elements are: 13–17 (α1), 21–29 (α2), 33–39 (β1), 48–52 (β2), 63–68 (β3), 70–78 (α3), 81–89 (β4), 112–120 (β5), 127–138 (β6), 141–151 (β7), 154–156 (β8), 157–172 (α4), 182–190 (β9), 195–200 (β10), 210–217 (α5), 222–224 (β11), and 229–236 (β12). Black domain covers pSEB(150–161) and p12(150–161) (see Table 1). Adapted from Swaminathan et al. [Swaminathan et al., Nature 359:801 (1992)].

FIG. 3 Lack of SEB agonist activity of SEB-derived peptides Aliquots of $4\times10^6$ PBMC were induced without inducer (−SEB), with SEB (+SEB), or with 1 μg/ml of one of the indicated SEB-related peptides (Table 1) as sole inducer. Total RNA was extracted after 4 h of induction and serial twofold dilutions were subjected to dot blot hybridization analysis with $^{32}$P-labeled IL-2 and IFN-γ anti-sense RNA probes. Autoradiograms were subjected to microdensitometry at 630 nm; $A_{630}$ is plotted.

FIGS. 4A–4B Antagonist activity of SEB-related peptides Aliquots of $4\times10^6$ PBMC were induced without inducer (−SEB), with SEB in the presence of no peptide (NP), or with SEB in the presence of 1 μg/ml of one of the indicated SEB-related peptides (sequences: Table 1). Total RNA was extracted after 4 hrs of induction and serial twofold dilutions (vertical rows) were subjected to dot blot hybridization analysis with $^{32}$P-labeled IL-2 and IFN-γ anti-sense RNA probes. Autoradiograms shown were quantitated by densitometry at 630 nm, plotted in (FIG. 4A). Fold inhibition (f.i.) of IL-2 and IFN-γ mRNA expression induced by SEB (FIG. 4B) was calculated from data as shown in (FIG. 4A), by subtracting basal levels of mRNA expressed (−SEB) and dividing extent of mRNA expression induced by SEB alone (NP) by that obtained with SEB in the presence of the indicated SEB-related peptide.

FIG. 5 Inhibition of SEB-mediated induction of IL-2 and IFN-γ mRNA by p12(150–161) Aliquots of $3\times10^7$ PBMC were induced with SEB, SEB-related peptides as indicated, or both. At times shown, total RNA was extracted and subjected to RNase protection analysis, using a $^{32}$P-labeled IL-2 or IFN-γ antisense RNA probe as for FIG. 1D. Autoradiograms are shown. Data for IL-2 and IFN-γ are derived from separate experiments.

Figure 6:
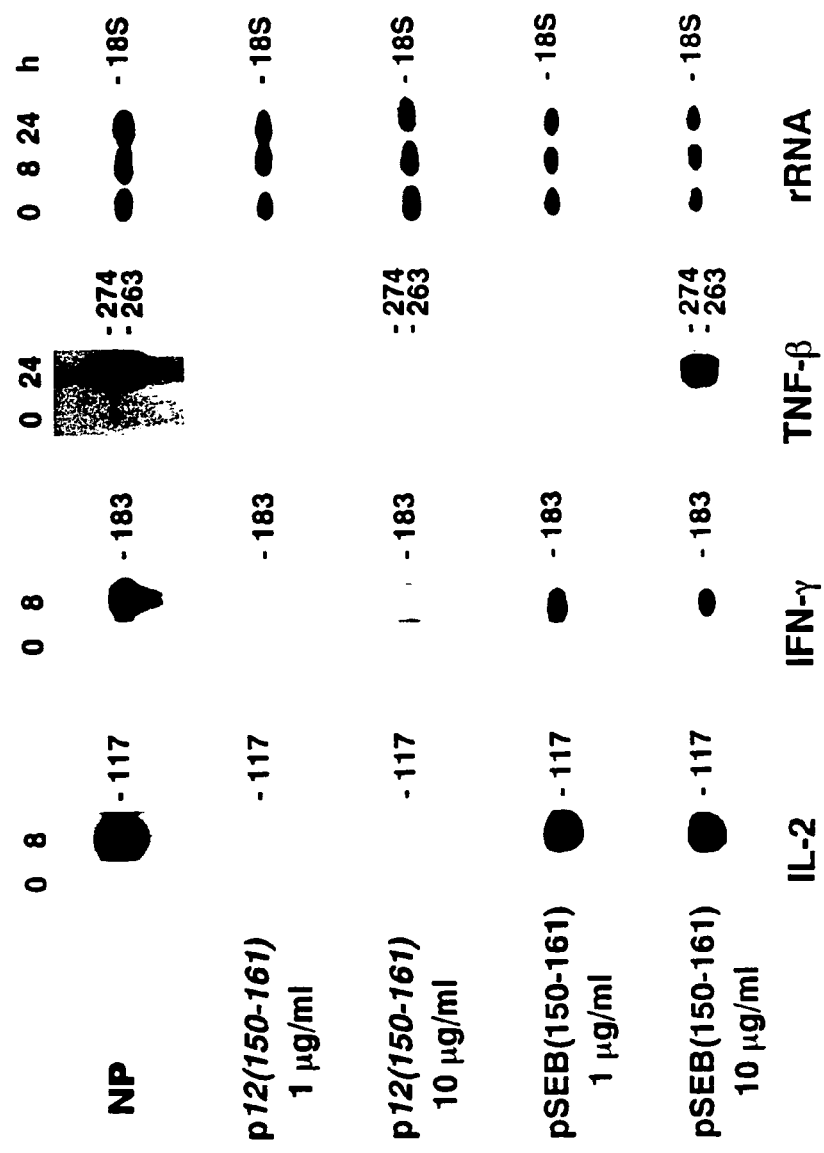

FIG. 6 Inhibition of SEB-mediated induction of IL-2, IFN-γ and TNF-β mRNA by p12(150–161) Aliquots of $3 \times 10^7$ PBMC were induced with SEB, in the presence of no peptide (NP) or of SEB-related peptides as indicated. At times shown, total RNA was extracted and subjected to RNase protection analysis, using a $^{32}$P-labeled IL-2, IFN-γ or TNF-β antisense RNA probe as for FIGS. 1D and 1E. rRNA served as loading control. Autoradiograms are shown.

Figure 7B:
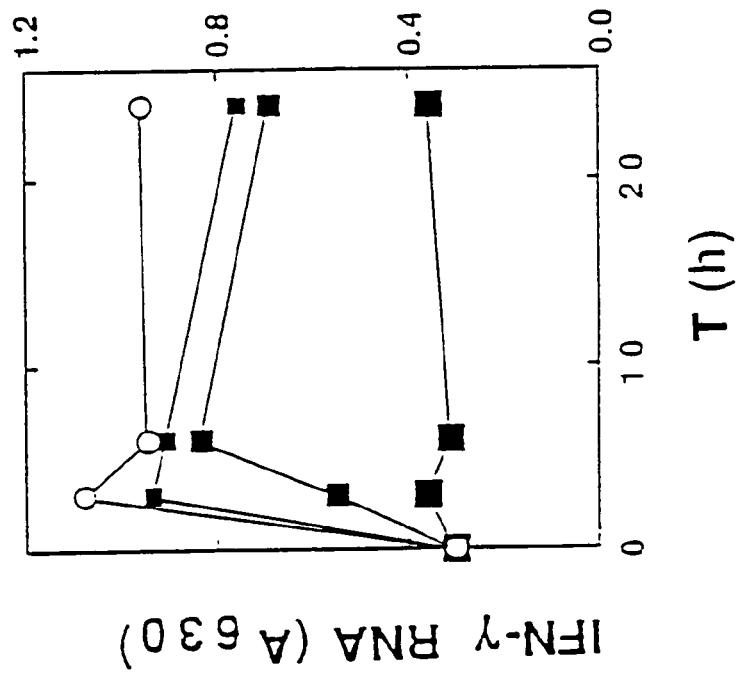
Figure 7A:
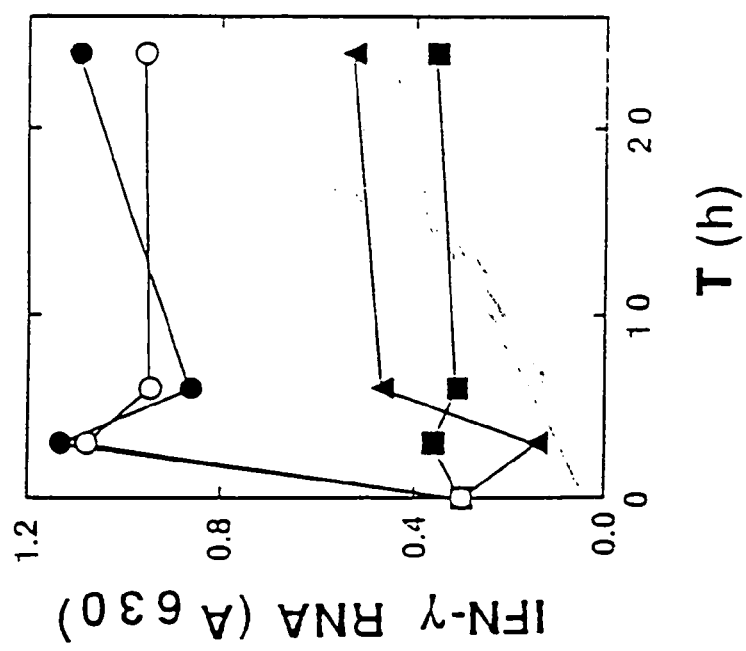

FIGS. 7A–7B SEB antagonist activity of p12(150–161) monomer, dimer and trimer (FIG. 7A) Aliquots of $4 \times 10^6$ PBMC were induced with 100 ng/ml of SEB alone (○), or with SEB in the presence of p12(150–161) monomer (●), dimer (■) or trimer (▲); molar excess of each peptide over SEB was 420-fold. (FIG. 7B) Dose response to dimer in the same experiment. Dimer was used at a concentration as in (FIG. 7A) (■) or diluted 1:10 (■) or 1:100 (■). At times indicated [T(h)], total RNA was extracted and serial twofold dilutions were subjected to dot blot hybridization analysis with $^{32}$P-labeled IFN-γ antisense RNA probe. Autoradiograms were subjected to micro-densitometry at 630 nm; $A_{630}$ is plotted.

Figure 8A:
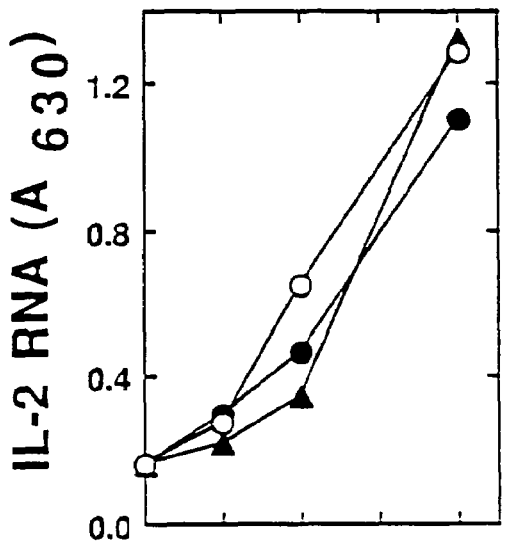
Figure 8B:
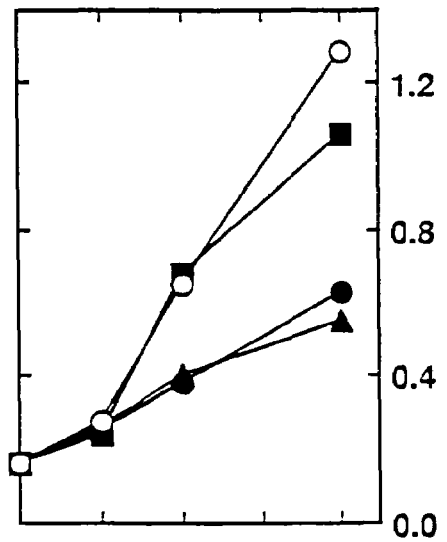
Figure 8C:
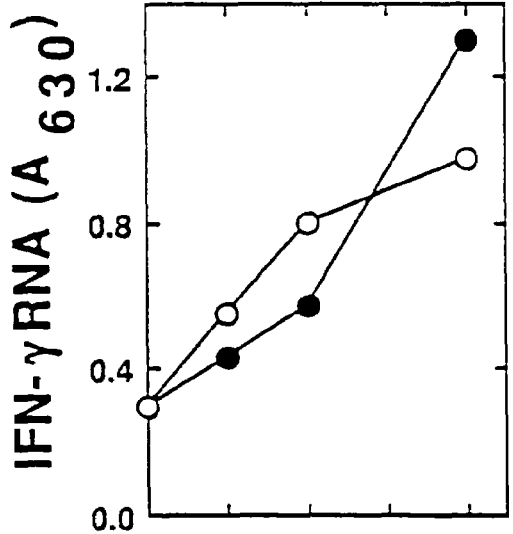
Figure 8D:
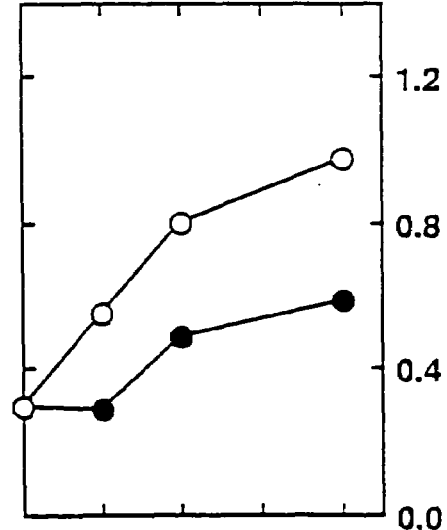

FIGS. 8A–8D SEB antagonist activity of Cys-p12 (150–161) Aliquots of $4 \times 10^6$ PBMC were induced with 100 ng/ml of SEB alone (○), or with SEB in the presence of undiluted peptide (▲) (in 420-fold molar excess over SEB), or of peptide diluted 1:10 (●) or 1:100 (■). In FIGS. 8A and 8C, p12(150–161) was used. In FIGS. 8B and 8D, Cys-p12 (150–161) was used, which is p12(150–161) carrying a Cys residue at both N- and C-termini. At times indicated [T(h)], total RNA was extracted and serial twofold dilutions were subjected to dot blot hybridization analysis with $^{32}$P-labeled IL-2 (FIGS. 8A and 8B), or IFN-γ (FIGS. 8C and 8D) antisense RNA probe. Autoradiograms were subjected to micro-densitometry at 630 nm; $A_{630}$ is plotted.

Figure 9:
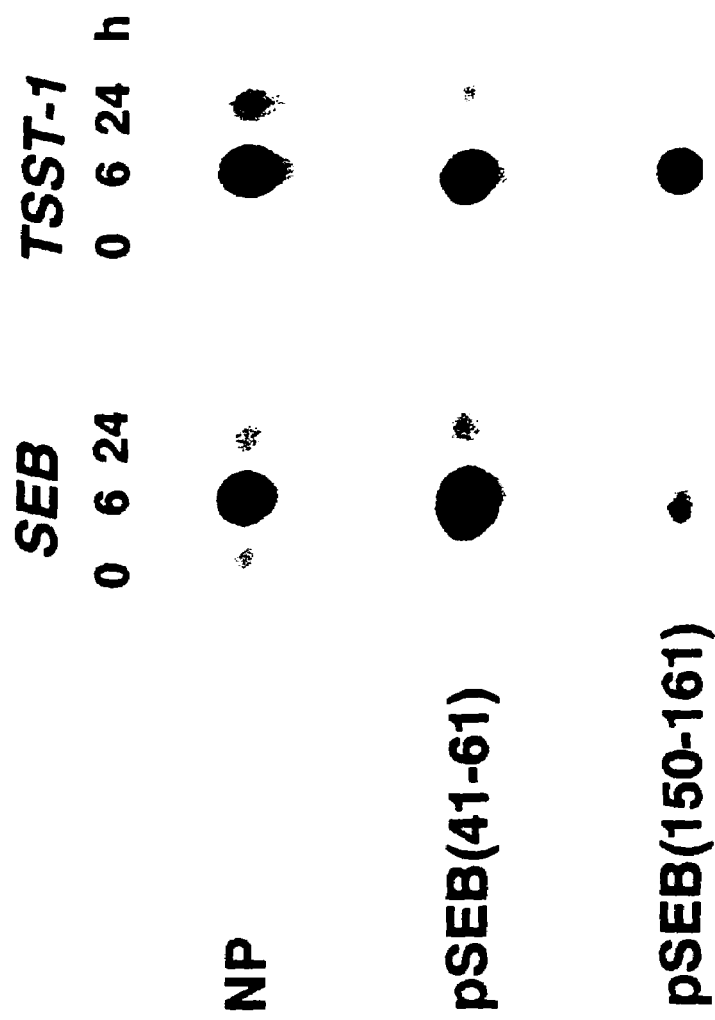

FIG. 9 Lack of antagonist activity of pSEB(150–161) for TSST-1 Aliquots of $3 \times 10^7$ PBMC were induced with SEB or TSST-1 as shown, in the presence of no peptide (NP) or of 1 μg/ml of pSEB(41–61) or pSEB(150–161) as indicated. At times shown (h), total RNA was extracted and subjected to RNase protection analysis, using a $^{32}$P-labeled IL-2 antisense RNA probe as for FIG. 1D.

FIGS. 10A–10D Lack of antagonist activity of p12 (150–161) for SEA Aliquots of $4 \times 10^6$ human PBMC were induced with SEB (FIGS. 10A, 10B) or SEA (FIGS. 10C, 10D), in the absence (○, △) or presence (●,▲) of 1 μg/ml of peptide p12(150–161). Total RNA was extracted at times [T(h)] indicated and serial twofold dilutions were subjected to dot blot hybridization analysis with $^{32}$P-labeled IL-2 (FIGS. 10A, 10C) and IFN-γ (FIGS. 10B, 10D) anti-sense RNA probes. Autoradiograms were quantitated by densitometry at 630 nm.

Figure 11:
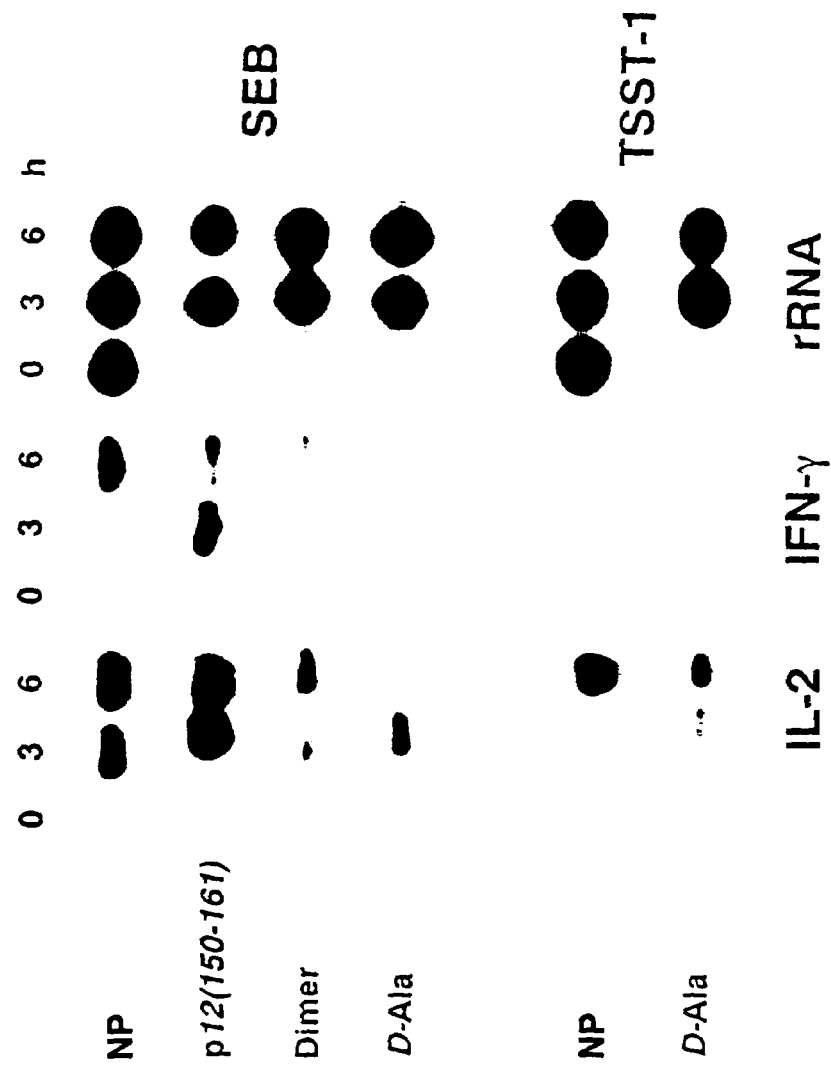

FIG. 11 Toxin antagonist activity of p12(150–161) dimer and D-Ala forms: SEB and TSST-1 Aliquots of $3 \times 10^7$ PBMC were induced with SEB or TSST-1 as indicated, in the presence of no peptide (NP) or of 10 μg/ml of p12 (150–161) or, where indicated, an equal molar concentration of p12(150–161) dimer (dimer) or of p12(150–161) carrying a D-Ala residue at both N- and C-termini (D-Ala). At times shown, total RNA was extracted and subjected to RNase protection analysis, using $^{32}$P-labeled IL-2 and IFN-γ antisense RNA probes as for FIG. 1D. rRNA served as loading control.

Figure 12A:
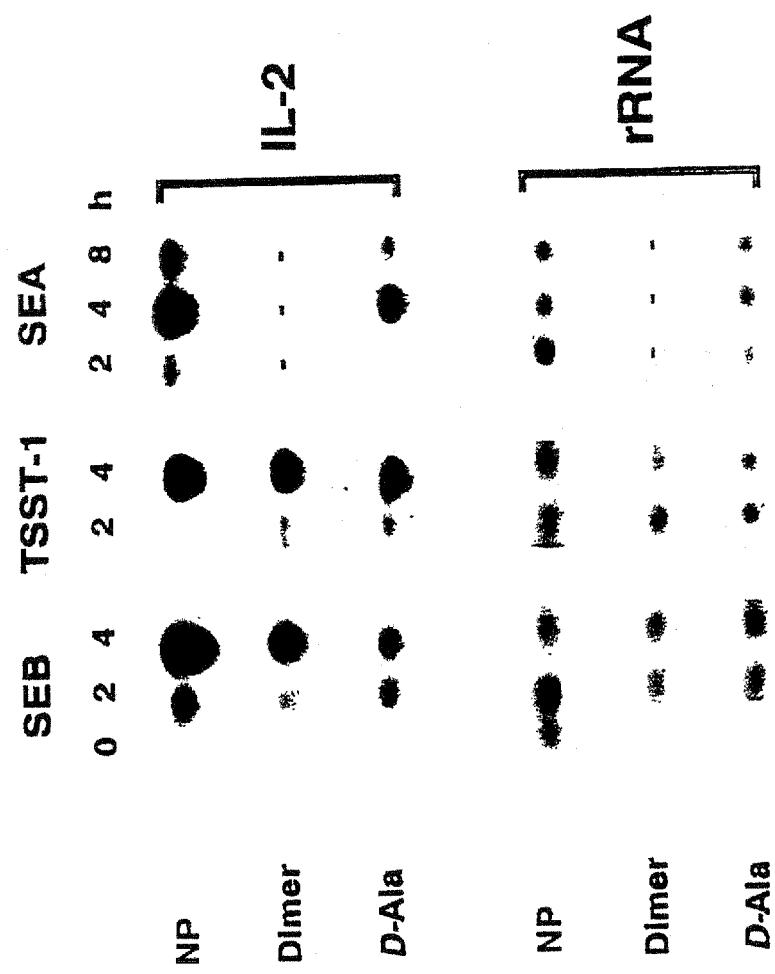

FIGS. 12A–12B Toxin antagonist activity of p12 (150–161) dimer and D-Ala forms: SEB, TSST-1, SEA and SPE A Aliquots of $3 \times 10^7$ PBMC were induced with SEB, TSST-1 or SEA as indicated, in the presence of no peptide (NP), p12(150–161) dimer (dimer) or p12(150–161) carrying a D-Ala residue at both N- and C-termini (D-Ala), each of the latter at a molar concentration equivalent to 10 μg/ml of p12(150–161) (FIG. 12A). At times shown, total RNA was extracted and subjected to RNase protection analysis, using $^{32}$P-labeled IL-2 antisense RNA probe as for FIG. 1D. rRNA served as loading control. In addition, aliquots of $3 \times 10^7$ PBMC were induced with 100 ng/ml of SPE A, in the presence of no peptide (NP) or of p12(150–161) carrying a D-Ala residue at both N- and C-termini (D-Ala) at a molar concentration equivalent to 10 μg/ml of p12(150–161) (FIG. 12B). At times shown, total RNA was extracted and subjected to RNase protection analysis, using $^{32}$P-labeled IL-2 antisense RNA probe as for FIG. 1D.

FIGS. 13A–13B Effect of anti-SEB peptide sera on induction of IL-2 and IFN-γ mRNA by SEB Aliquots of $4 \times 10^6$ PBMC were induced with SEB (control, C) (●). Rabbit sera against SEB peptides p12LC(150–161) (▲), pSEBLC (13–33) (○), pSEB(81–93) (□) or pSEB(41–61) (■) in 1:100 dilution were included from the onset of induction. At times [T(h)] indicated, total RNA was extracted and serial twofold dilutions (vertical rows) were subjected to dot blot hybridization analysis with $^{32}$P-labeled IL-2 (FIG. 13A) and IFN-γ (FIG. 13B) anti-sense RNA probes. Only autoradiograms for IL-2 are shown. Autoradiograms were quantitated by densitometry at 630 nm (FIGS. 13A, 13B).

FIG. 14A–14B Effect of anti-SEB peptide sera on induction of IL-2 and IFN-γ mRNA by SEA Aliquots of $4 \times 10^6$ PBMC were induced with SEA (control, C). Where shown, rabbit sera against SEB peptides p12LC(150–161), pSEBLC (13–33), pSEB(81–93) or pSEB(41–61) in 1:100 dilution were included from the onset of induction. At 6 hrs (FIG. 14A) and 20 hrs (FIG. 14B), total RNA was extracted and serial twofold dilutions (vertical rows) were subjected to dot blot hybridization analysis with $^{32}$P-labeled IL-2 (FIG. 14A) and IFN-γ (FIG. 14B) anti-sense RNA probes; autoradiograms shown were quantitated by densitometry at 630 nm.

Figure 15A:
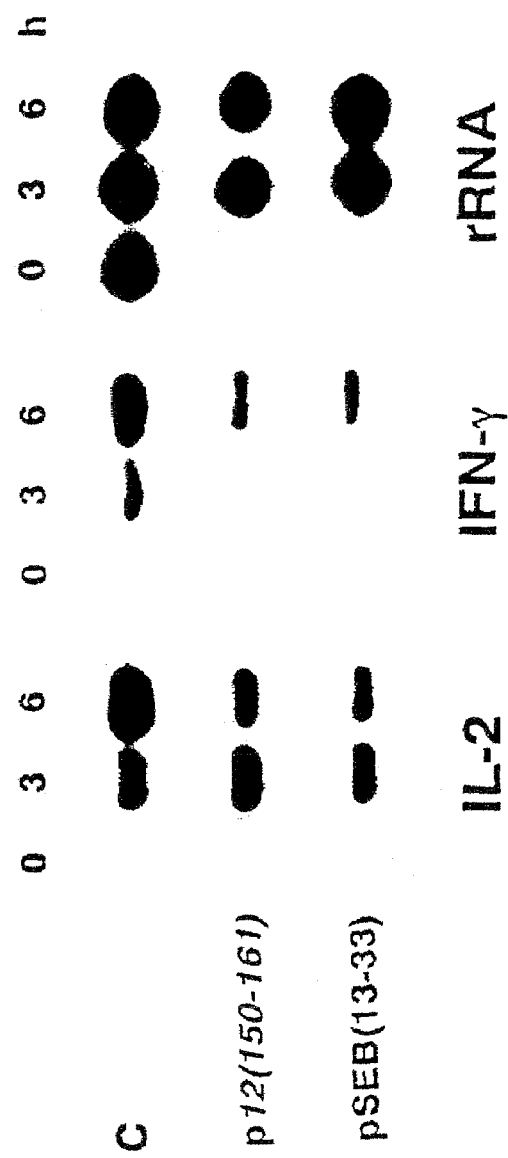
Figures 12B, 15B:
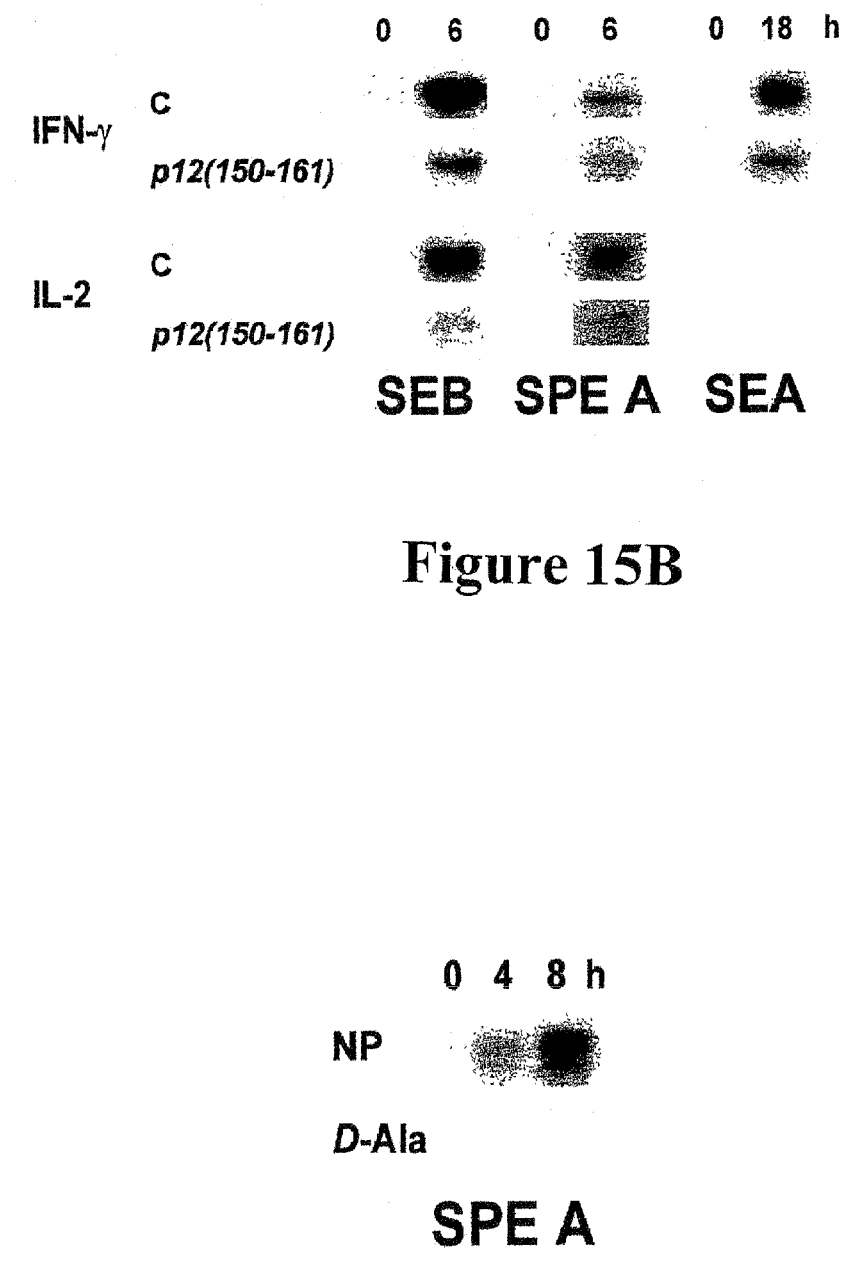

FIGS. 15A–15B Effect of anti-SEB peptide sera on induction of IL-2 and IFN-γ mRNA by TSST-1, SEB, SPEA or SEA Aliquots of $3 \times 10^7$ PBMC were induced with 100 ng/ml of TSST-1 (control, (C)) (FIG. 15A). Where shown, rabbit sera against SEB peptides p12LC(150–161) or pSEBLC (13–33) in $1:10^4$ dilution were included from the onset of induction. At times shown, total RNA was extracted and subjected to RNase protection analysis, using $^{32}$P-labeled IL-2 and IFN-γ antisense RNA probes as for FIG. 1D. rRNA served as loading control. In addition, aliquots of $3 \times 10^7$ PBMC were induced with 100 ng/ml of SEB, SPE A or SEA (control, (C)) (FIG. 15B). Where shown, rabbit serum against SEB peptide p12LC(150–161) in $1:10^4$ dilution was included from the onset of induction. At times shown, total RNA was extracted and subjected to RNase protection analysis, using $^{32}$P-labeled IL-2 and IFN-γ antisense RNA probes as for FIG. 1D; for SEA, only the IL-2 probe was used.

FIG. 16 Protection of mice from the lethal effect of a low dose of SEB by p12(150–161) carrying a D-Ala residue at both N- and C-termini Groups of 10 mice each (9–10 week BALB/C females) were injected intraperitoneally with 20 mg per mouse of D-galactosamine. Two hours later, one group (filled triangles) received 5 μg per mouse of p12 (150–161) carrying a D-Ala residue at both N- and C-termini (p12), by intravenous injection. Thirty minutes later, each mouse received 20 μg of SEB by intraperitoneal administration. Survival in each group was determined thereafter, at the times in hours indicated. Surviving animals showed no signs of malaise and were indistinguishable from normal controls in behavior; they survived for as long as monitored, two weeks.

FIG. 17 Protection of mice from the lethal effect of SEB by p12(150–161) carrying a D-Ala residue at both N- and C-termini Groups of 10 mice each (9–10 week BALB/C females) were injected intraperitoneally with 20 mg per mouse of D-galactosamine. Two hours later, 25 μg per mouse of p12 (see FIG. 16) were administered to one group by intravenous injection (▲) and to a second group by intraperitoneal administration (Δ). Control group mice did not receive peptide (■). Thirty minutes later, each mouse received 20 μg of SEB by intraperitoneal administration. Survival in each group was determined thereafter, at the times in hours indicated. Surviving animals showed no signs of malaise and were indistinguishable from normal controls in behavior; they survived for as long as monitored, two weeks.

Figure 18:
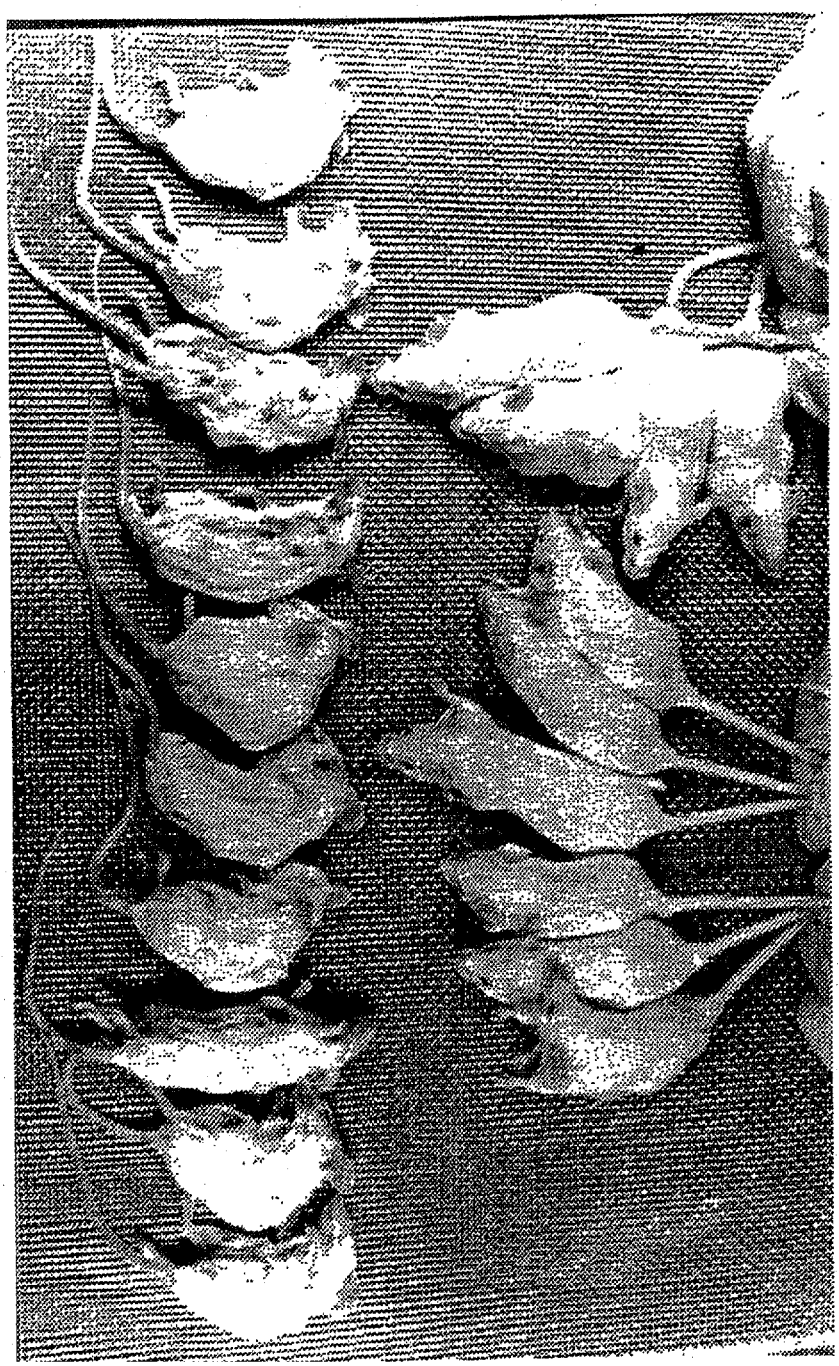

FIG. 18 Protection of mice from the lethal effect of SEB by p12(150–161) carrying a D-Ala residue at both N- and C-termini Photograph of two groups of 10 mice from the experiment of FIG. 17, taken two weeks after challenge with SEB. Top group: mice that received 25 μg of p12 (see FIG. 16) by intravenous injection before challenge with SEB. Bottom group: mice that did not receive peptide before challenge with SEB.

Figure 19:
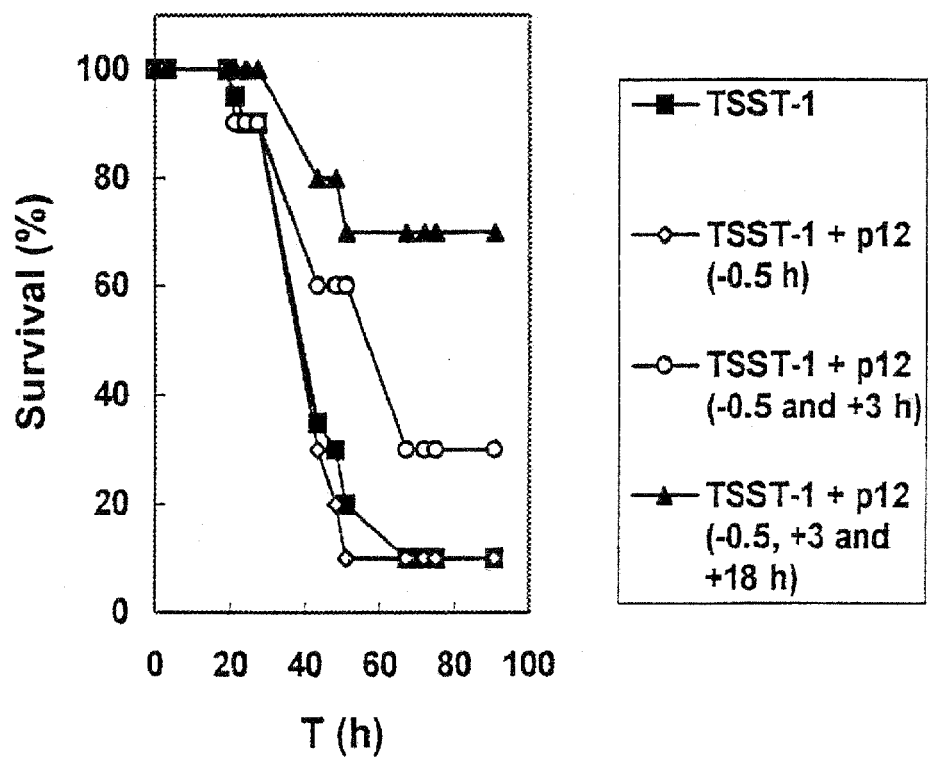

FIG. 19 Protection of mice from the lethal effect of TSST-1 by p12(150–161) carrying a D-Ala residue at both N- and C-termini Groups of 10 mice each (9–10 week BALB/C females) were injected intraperitoneally with 40 mg per mouse of D-galactosamine. Two hours later, 25 μg per mouse of p12 (see FIG. 16) were administered by intravenous injection to each group (✦, ○, ▲) except a control group of 20 mice (■). Thirty minutes later, each mouse received 5 μg of TSST-1 by intraperitoneal administration. An additional intravenous injection of 25 μg per mouse of p12 was administered at 3 hr post-challenge (○) or at 3 and 18 hr post-challenge (▲). Survival in each group was determined thereafter, at the times in hours indicated. Surviving animals showed no signs of malaise and were indistinguishable from normal controls in behavior; they survived for as long as monitored, two weeks.

DETAILED DESCRIPTION OF THE INVENTION

In search for efficient agents for long and short term treatment and prophylaxis of toxic shock induced by pyrogenic exotoxins, a series of short peptides related to certain domains within the SEB protein molecule has been designed. The biological properties of different synthetic SEB-related peptides were then evaluated by the following several criteria:

1. Lack of SEB agonist activity, assayed by the ability to induce in peripheral blood mononuclear cells from normal human blood donors (PBMC) the expression of mRNA encoded by the IL-2 and IFN-γ genes, in the absence of any other inducing agent;
2. pyrogenic exotoxin antagonist activity, assayed by the ability to inhibit, in PBMC, the expression of mRNA encoded by the IL-2, IFN-γ, and TNF-β genes induced by a pyrogenic exotoxin such as SEB;
3. Immunogenicity, assayed by the ability of a peptide to elicit, in immunized rabbits, the production of immunoglobulin G (IgG) antibodies that bind SEB;
4. Immunogenicity, assayed by the ability of a peptide to elicit, in immunized rabbits, the production of antibodies that block the harmful action of pyrogenic exotoxins, such as SEB on the human cellular immune response, monitored by the ability of rabbit serum raised against a peptide to inhibit, in PBMC, the induction of IL-2 and IFN-γ mRNA by SEB or by other pyrogenic exotoxins such as TSST-1 or the more related toxin, SEA;
5. Activity of a vaccine, such as anti-SEB vaccine, assayed by the ability of a peptide to protect immunized animals, in the D-galactosamine mouse model, against lethal doses of SEB whether administered via the intramuscular or intranasal route.

The inventors have indeed obtained peptides that meet each of these five criteria. In a specific embodiment of the invention, a SEB-related dodecapeptide antagonist was designed. This peptide blocks the action of SEB as well as other pyrogenic exotoxins on the human immune response in vitro, severely inhibiting SEB-mediated induction of IL-2, IFN-γ and TNF-β mRNA. It is clear that this peptide could be used for treatment of acute toxic shock and of harmful effects which may be due to, for example, accidental food poisoning induced by pyrogenic exotoxins.

In addition, this peptide elicits antibodies that protect human lymphoid cells against SEB, SEA, and TSST-1, indicating that it may confer wider protective immunity against pyrogenic toxins. However, antibodies raised against peptides derived from certain other SEB protein domains actually enhanced the response of human PBMC to SEB and SEA, as expressed by greater induction of IL-2 and IFN-γ mRNA, rather than protecting against the toxins. Immunization of mice with the SEB antagonist peptide elicited protection against lethal doses of SEB, resulting in survival of test animals. It is clear that the peptide may also be used for conferring long-term immunity against toxic shock induced by pyrogenic exotoxins.

Thus, in a first aspect, the present invention relates to peptides comprising an amino acid sequence substantially homologous to the amino acid sequence of a fragment of a pyrogenic exotoxin, and to functional derivatives of such peptides, capable of eliciting protective immunity against toxic shock induced by the exotoxins. The terms derivatives and functional derivatives used herein mean peptides with any insertions, deletions, substitutions and modifications that are capable of eliciting protective immunity against toxic shock induced by the exotoxins and/or of antagonizing toxin-mediated activation of T cells (hereafter referred to as "derivative/s").

In a second aspect the invention relates to peptides comprising an amino acid sequence substantially homologous to the amino sequence of a fragment of a pyrogenic exotoxin, and to derivatives of such peptides, capable of antagonizing toxin-mediated activation of T cells. The peptides of the invention are capable of protecting against toxic shock induced by a pyrogenic exotoxin or by a mixture of pyrogenic exotoxins.

The pyrogenic exotoxin is usually a bacterial exotoxin, specifically an exotoxin produced by *Staphylococcus aureus* or by *Streptococcus pyogenes*.

In a preferred embodiment of both said aspects of the invention, the invention relates to a peptide comprising an amino acid sequence substantially homologous to the amino sequence of a fragment of *Staphylococcal aureus* enterotoxin B (SEB).

In a specifically preferred embodiment the invention relates to peptides comprising the amino acid sequence shown in SEQ ID NO:1 (positions 150 to 161 of the sequence of the naturally occurring SEB protein shown in SEQ ID NO:12), and functional derivatives thereof, capable of eliciting protective immunity against toxic shock induced by at least one pyrogenic exotoxin and/or of antagonizing toxin-mediated activation of T cells. This peptide is also capable of protecting against toxic shock induced by a pyrogenic exotoxin or by a mixture of pyrogenic exotoxins. These peptides can therefore be used for both immediate treatment of acute toxic shock and of the harmful effects which may be due to, for example, accidental food poisoning, induced by the pyrogenic exotoxins and for conferring long-term immunity against such toxic shock.

A particular example may be a peptide having the amino acid sequence shown in SEQ ID NO:1 (hereafter also referred to as pSEB(150–161)) and functional derivatives thereof. This peptide is capable of eliciting protective immunity against toxic shock induced by at least one pyrogenic exotoxin and/or of antagonizing toxin-mediated activation of T cells.

In an alternative embodiment the invention relates to peptides comprising the amino acid sequence shown in SEQ ID NO:2 and to derivatives thereof, capable of eliciting protective immunity against toxic shock induced by at least one pyrogenic exotoxin and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock. A particular example may be a peptide having the amino acid sequence shown in SEQ ID NO:2 (hereinafter also referred to as p12(150–161)) and derivatives thereof capable of eliciting protective immunity against toxic shock induced by at least one pyrogenic exotoxin and/or of antagonizing toxin-mediated activation of T cells.

In a further embodiment the invention relates to peptides comprising the amino acid sequence shown in SEQ ID NO:3 (positions 152 to 161 of the sequence of the naturally occurring protein shown in SEQ ID NO:12) and to functional derivatives thereof, capable of eliciting protective immunity against toxic shock induced by at least one pyrogenic exotoxin and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock.

Particular examples may be a peptide having the amino acid sequence shown in SEQ ID NO:3 (hereinafter also referred to as pSEB(152–161)) and derivatives thereof capable of eliciting protective immunity against toxic shock induced by a pyrogenic exotoxin or a mixture of pyrogenic exotoxins and/or of antagonizing toxin-mediated activation of T cells.

In addition, the invention relates to peptides comprising the amino acid sequence shown in SEQ ID NO:4 and to functional derivatives thereof, capable of eliciting protective immunity against toxic shock induced by at least one pyrogenic exotoxin and/or of antagonizing toxin-mediated activation of T cells. Also these peptides can be used for both immediate treatment of acute toxic shock and of the harmful effects which may be due to, for example, accidental food poisoning induced by the pyrogenic exotoxins and for conferring long-term immunity against such toxic shock.

A particular example may be a peptide having the amino acid sequence shown in SEQ ID NO:4 (hereinafter also referred to as p10(152–161)) and functional derivatives thereof, capable of eliciting protective immunity against toxic shock induced by a pyrogenic exotoxin or a mixture of pyrogenic exotoxins and/or of antagonizing toxin-mediated activation of T cells.

As mentioned, pSEB(150–161) corresponds to the natural amino acid sequence in SEB between positions 150–161, while p12(150–161) differs from the corresponding natural amino acid sequence of SEB in 3 out of the 12 positions, yet possesses even greater toxin antagonist activity. It is thus possible to design a pyrogenic exotoxin antagonist and/or vaccine through use of short peptides related, but not necessarily identical to, domains within the SEB toxin molecule.

The lack of structure of linear peptides on one hand renders them vulnerable to proteases in human serum and on the other hand acts to reduce their affinity for target sites, because only few of the possible conformations may be active. Therefore, it is desirable to optimize antagonist peptide structure.

Thus, the peptides of the invention can be coupled through their N-terminus to a lauryl-cysteine (LC) residue and/or through their C-terminus to a cysteine (C) residue, or to other residue/s suitable for linking the peptide to adjuvant/s for immunization, as will be described in more detail hereafter.

Accordingly, in a further embodiment, the invention relates to a peptide having the amino acid sequence shown in SEQ ID NO:5 (hereinafter also referred to as pSEBLC (150–161)) and functional derivatives thereof, capable of eliciting protective immunity against toxic shock induced by pyrogenic exotoxins and/or of antagonizing toxin-mediated activation of T cells. These peptides can also be used for both immediate treatment of acute toxic shock and of the harmful effects which may be due to, for example, accidental food poisoning induced by the pyrogenic exotoxins and for conferring long-term immunity against such toxic shock.

In yet another embodiment, the invention relates to a peptide having the following amino acid sequence shown in SEQ ID NO:6 (hereinafter also referred to as p12LC (150–161)) and functional derivatives thereof capable of eliciting protective immunity against toxic shock induced by pyrogenic exotoxins and/or of antagonizing toxin-mediated activation of T cells. Evidently, such peptides can also be used for both immediate treatment of acute toxic shock and of the harmful effects which may be due to, for example, accidental food poisoning induced by the pyrogenic exotoxins and for conferring long-term immunity against such toxic shock.

The peptides of the invention, as well as the derivatives thereof may all be positively charged, negatively charged or neutral and may be in the form of a dimer, a multimer or in a constrained conformation.

A constrained conformation can be attained by internal bridges, short-range cyclizations, extension or other chemical modification.

Peptides in the form of a dimer or trimer can have, for example, the amino acid sequences shown in SEQ ID NOs. 7 and 8, respectively (hereinafter also referred to as Dimer and Trimer, receptively) and functional derivatives thereof, capable of eliciting protective immunity against toxic shock induced by pyrogenic exotoxins and/or of antagonizing toxin-mediated activation of T cells. As with other peptides of the invention, these peptides can also be used for both immediate treatment of acute toxic shock and of the harmful effects caused thereby and for conferring long-term immunity against such toxic shock.

Further, the peptides of the invention may be extended at the N-terminus and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. A preferred synthetic amino acid residue is D-alanine.

A particular example for a peptide extended with synthetic amino acid residues is the peptide having the amino acid sequence shown in SEQ ID NO:10 (hereinafter also referred to as D-Ala) and functional derivatives thereof, capable of eliciting protective immunity against toxic shock induced by pyrogenic exotoxins and/or of antagonizing toxin-mediated activation of T cells.

An additional example for such an extension is provided by peptides extended both at the N-terminus and/or C-terminus thereof with a cysteine residue. Naturally, such an extension may lead to a constrained conformation due to Cys—Cys cyclization resulting from the formation of a disulfide bond. A particular such peptide has the amino acid sequence shown in SEQ ID NO:9 (hereinafter also referred to as Cys-p12(150–162)) and functional derivatives thereof, capable of eliciting protective immunity against toxic shock induced by pyrogenic exotoxins and/or of antagonizing toxin-mediated activation of T cells. According to one embodiment of the invention, the Cys-p12(150–162)) is a cyclic peptide having a disulfide bond via the terminal cysteine residues. Nevertheless, the Cys-p12(150–162) peptide may be linear.

In addition the peptide may be extended by aromatic amino acid residue/s, which may be naturally occurring or synthetic amino acid residue/s. A preferred aromatic amino acid residue is tryptophan. Alternatively, the peptides can be extended at the N-terminus and/or C-terminus thereof with amino acids present in corresponding positions of the amino acid sequence of the naturally occurring pyrogenic exotoxin.

Nonetheless, according to the invention, the peptides of the invention may be extended at the N-terminus and/or C-terminus thereof with various identical or different organic moieties which are not a naturally occurring or synthetic amino acids. As an example for such extension, the peptide may be extended at the N-terminus and/or C-terminus thereof with an N-acetyl group. A particular example for such an extension is the peptide having the amino acid sequence shown in SEQ ID NO:11 (hereinafter also referred to as Ac-p12(150–161)) and functional derivatives thereof, capable of eliciting protective immunity against toxic shock induced by pyrogenic exotoxins and/or of antagonizing toxin-mediated activation of T cells.

These extended peptides, as other peptides of the invention, can also be used for both immediate treatment of acute toxic shock and of the harmful effects caused thereby and for conferring long-term immunity against such toxic shock.

The peptides of the invention are capable of inhibiting expression of pyrogenic toxin-induced mRNA encoded by the IL-2, IFN-γ or TNF-β genes, as will be shown in the following Examples.

In addition, the peptides of the invention are capable of eliciting the production of antibodies that block T-cell activation in immunized individuals. The production of antibodies will be enhanced in the presence of a suitable immunization adjuvant. Preferred adjuvants may be keyhole lympet hemocyanin (KLH), proteosomes or alum.

As will be shown in the Examples, peptide p12(150–161) and the specific derivatives thereof, i.e. the Dimer form, the Cys form (Cys-p12(150–161)) and D-Ala form exhibit antagonist activity against SEB as well as against other pyrogenic exotoxins. The amino acid sequence of these synthetic peptides having the sequence shown in SEQ ID NOs.:2, 7, 9 and 10, differ in several positions from the corresponding sequence in SEB, T N KK K V T A QELD, found in peptide pSEB(150–161). The K K K and Q E L D motifs, features shared by peptides p12(150–161) (and its derivatives) and pSEB(150–161), are spaced equally in both and may be important for antagonist activity, with the triple-lysine motif K K K conferring 3 positive charges. Residues T150, K152, E159 and D161 of this SEB domain are conserved among all staphylococcal enterotoxins [Swaminathan et al. (1992) ibid.]. Indeed, the 150–161 domain of SEB is highly conserved among pyrogenic toxins in general, with 10/12 identities for SEA, SEC1, SEC2, and S. pyogenes exotoxm A (SPEA) and 9/12 for SEE [Bohach and Schilevert, Mol Gen Genet 209:5 (1987); Couch et al., J Bacteriol 170:2954 (1988); Bohach and Schijevert, Infect Immun 57:2249 (1989)]. All of these toxins contain the residues underlined above, including the first 2 lysine residues (KK) and the QELD [Swaminathan et al. (1992) ibid.; Bohach and Schlievert (1987) ibid.; Couch et al. (1988) ibid.; Bohach and Schlievert (1989) ibid.]. The superantigen, pep M5 protein, also contains a region with limited homology (<50%) to pSEB(150–161) located near its C-terminus [Wang et al., J Inimunol 151:1419 (1993)].

Conservation of SEB domains among the pyrogenic toxin family is, however, not unique for amino acids 150–161. SEB domains covering amino acids 76–86, 113–124, 151–168 and 213–226 all show extensive conservation within this family [Hoffmann et al., Infect Immun 62:3396 (1994)]. Moreover, the relevance of the conservation of the above-mentioned motifs corresponding to part of the sequence in pSEB(150–161) is not clear, since this region does not contribute to mitogenicity [Wang et al. (1993) ibid.].

In a further aspect, the invention relates to pharmaceutical compositions for the treatment or prophylaxis of toxin-mediated activation of T cells, comprising as active ingredient a therapeutically effective amount of at least one peptide according to the invention or derivative thereof. As described above, the peptides comprise an amino acid sequence substantially homologous to the amino acid sequence of a fragment SEB. The pharmaceutical compositions of the invention are also useful in protecting against toxic shock induced by a pyrogenic exotoxin or by a mixture of pyrogenic exotoxins.

The term toxin-mediated activation as used throughout this application can mean activation of T cells mediated by a single pyrogenic exotoxin or a mixture of such toxins.

Examples 4, 5, 6 and most remarkably the in vivo murine experiments described in Example 9 and FIGS. 16 to 19, show that it is possible to design an effective pyrogenic exotoxin antagonist pharmaceutical composition, which contains as active ingredient a peptide according to the invention, and acts as a broad-spectrum antagonist of pyrogenic exotoxins. Thus, for example, the p12(150–151) peptide carrying D-Ala residues at both its N- and C-termini, which is SEB-related, afforded good antagonist activity not only against SEB-induced toxic shock, but also against toxic shock induced by the remotely homologous TSST-1.

The pharmaceutically 'effective amount' for purposes herein is that determined by such considerations as are known in the art. The amount must be sufficient to antagonize toxin-mediated activation of T cells.

The pharmaceutical composition of the invention can be prepared in dosage units forms and may be prepared by any of the methods well-known in the art of pharmacy. In addition, the pharmaceutical compositions of the invention may further comprise pharmaceutically acceptable additives such as pharmaceutical acceptable carrier, excipient or stabilizer, and optionally other therapeutic constituents. Naturally, the acceptable carriers, excipients or stabilizers are non-toxic to recipients at the dosages and concentrations employed.

The magnitude of therapeutic dose of the composition of the invention will of course vary with the group of patients (age, sex, etc.), the nature of the condition to be treated and with the route administration and will be determined by the attending physician.

In yet a further embodiment, the invention relates to vaccines for conferring immunity against toxic shock induced by pyrogenic exotoxins, comprising as active ingredient an immunologically effective amount of at least one peptide according to the invention or derivatives thereof and may contain mixtures of such peptides and derivatives.

By the term 'immunologically effective amount' is meant any amount sufficient to enhance the production of antibodies that block T cell activation induced by pyrogenic exotoxins, and confer immunity against toxic shock induced by a pyrogenic exotoxin or by a mixture of pyrogenic exotoxins.

The vaccines of the invention may optionally further comprise suitable immunization adjuvants or mixtures thereof. Suitable adjuvants may be proteosomes, KLH and alum, as well as combinations of proteosomes with alum and of KLH with alum.

As will be shown in the following Examples, the vaccines according to the invention are capable of enhancing production of antibodies that block T-cell activation induced by pyrogenic exotoxins.

Efforts to develop antidotes for use against toxic shock symptoms have concentrated on blocking downstream phenomena in the toxicity cascade, mainly by inhibiting the action of TNF with monoclonal antibodies or soluble receptors. The high levels of cytokines produced in response to toxins render this approach ineffective. The present Invention shows that it is possible to block the action of a pyrogenic exotoxin by an altogether different strategy, using antagonists that inhibit toxin action at the top of the toxicity cascade, before activation of T cells takes place.

The Examples describe in detail molecular methods, analysis of pyrogenic exotoxin-mediated activation of the human cellular immune response through expression of IL-2, IFN-γ, and TNF-β genes in PBMC, to evaluate toxin antagonist activity.

Studies in human PBMC were combined with animal tests to evaluate immunogenic properties and vaccine efficacy and it will be shown that these methods are applicable in devising agents that counteract or protect human PBMC also against other members of the family of pyrogenic exotoxins.

Because humans are far more sensitive to pyrogenic exotoxins than mice, while primate models poses other limitations such as cost, there is a need for a human in vitro system, capable of analyzing the mechanisms of toxin-mediated activation and suppression of the immune response. The present invention provides such a system, which offers major advantages:

a) The experimental system employs freshly prepared human lymphoid cell populations that preserve cell-cell interactions involved in regulation of cytokine production and are as close as possible to the peripheral immune system of the body;
b) Early events of the immune response can be analyzed precisely and directly by following the transient and highly regulated expression of IL-2, IFN-γ and TNF-β mRNA;
c) Expression of IL-2, IFN-γ and TNF-β genes is exquisitely sensitive to activation elicited by SEB;
d) This molecular approach is far more direct and specific than measurement of biological responses, such as cell proliferation or antibody production, that are the cumulative result of a sequence of events;
e) The approach presented offers a tool for mapping functional domains in SEB essential for activation of human IL-2, IFN-γ and TNF-β genes, and can serve to facilitate both antagonist and vaccine development.

Thus, the invention also relates to a method for treating toxic shock induced by a pyrogenic exotoxin or a mixture of pyrogenic exotoxins. The method comprises administering to a patient in need of such treatment a therapeutically effective amount of the pharmaceutical composition of the invention or a therapeutically effective amount of at least one peptide of the invention, or functional derivative thereof.

In a further embodiment there is provided a method for preventing toxic shock induced by a pyrogenic exotoxin or a mixture of pyrogenic exotoxins comprising administering to a patient in need of such treatment a therapeutically effective amount of a composition of the invention or of a therapeutically effective amount of at least one peptide of the invention or functional derivative thereof.

The invention also relates to a method for immunizing a patient against toxic shock induced by pyrogenic exotoxin, comprising administering to a patient an effective immunizing amount of the vaccine of the invention or of at least one peptide of the invention or functional derivative thereof.

The magnitude of therapeutic dose of the peptide or of the vaccine of the invention will of course vary with the group of patients (age, sex etc.), the nature of the condition to be treated and with the route administration and will be determined by the attending physician.

The peptides and the vaccines of the invention can be administered and dosed in accordance with good medical practice. In particular, the immunization method of the invention comprises a single administration of the peptides or vaccines of the invention. Administration may be carried out in various ways, including intravenous, intramuscular or subcutaneuos injection. However, other methods of administration such as intranasal administration are also possible.

As shown hereafter, antibodies raised against peptides derived from certain SEB protein domains actually enhance the response of human PBMC to SEB and SEA, as expressed by induction of IL-2 and IFN-γ mRNA, rather than protect against these toxins. This would provide a tool for detecting such potential exacerbation by any pyrogenic exotoxin vaccine even before trials with humans are conducted.

Design of pyrogenic exotoxin antagonist peptides as described herein may find novel applications not only in hitherto neglected areas, prophylaxis against pyrogenic exotoxins and treatment of toxin-exposed individuals but also may facilitate the development of a safer pyrogenic exotoxin vaccine. A defined peptide vaccine, free of exacerbating properties, would be superior to a toxoid vaccine.

Thus, the invention also relates to antibodies directed against a peptide of the invention, which are capable of blocking T-cell activation by a pyrogenic exotoxin or a mixture of pyrogenic exotoxins, which may be mono- or polyclonal antibodies.

In addition, the invention also relates to antisera containing antibodies directed against peptides of the invention. For example, peptides such as pSEBLC(150–161) or p12LC (150–161) can be linked through the lauryl cysteine residue to proteosomes. Alternatively, peptides such as those coupled through their C-terminus to a cysteine (C) residue, as described above, can be linked through the cysteine residue to KLH. KLH and proteosomes are known adjuvants for immunization and the peptides so linked are capable of eliciting the production of antibodies.

It is also known in the art that aluminum hydroxide (alum) may be used as an immunization adjuvant directly, with non-linked peptides, or after linking a peptide to proteosomes or to KLH [Lowell et al., (1996) ibid.] or other suitable adjuvants. Therefore, the invention also relates to antisera containing antibodies directed against peptides of the invention, or functional derivatives thereof. The antisera of the invention are capable of alleviating toxic shock induced by a pyrogenic exotoxin. An antiserum according to the invention can be a domestic animal antiserum, for example rabbit, sheep, bovine, equine, porcine or goat antiserum.

For some purposes, for example the in vitro use mentioned above, human sera from immunized individuals can be used.

As already mentioned above, at present there exists no tool for assessing the efficacy of a vaccine against pyrogenic toxins in conferring immunity thereagainst. The present invention provides for such a method and thus, in a further aspect the invention relates to a method for assessing the efficacy of a vaccine for conferring immunity against one or more pyrogenic toxins comprising determining the ability of serum from an immunized individual to antagonize toxin-mediated activation of T cells.

The ability of serum from an immunized individual to antagonize toxin-mediated activation of T cells can be determined by measuring the inhibition of expression of pyrogenic toxin-induced mRNA encoded by the IL-2, IFN-γ, or TNF-β genes. Reference may be made to Example 7 and FIGS. 13 to 15.

A kit for assessing the efficacy of a vaccine for conferring immunity against one or more pyrogenic toxins comprising determining the ability of serum from an immunized individual to antagonize toxin-mediated activation of T cells by the method of the invention is also provided.

EXAMPLES

Cell Culture and Induction of Human Cytokine Gene Expression

PBMC from healthy human donors were separated on Ficoll Paque (Pharmacia), washed twice with 50 ml of RPMI 1640 medium, resuspended at a density of $4\times10^{6}$/ml and cultured in this medium supplemented with 2% fetal calf serum, 2 mM glutamine, 10 mM MEM nonspecific amino acids, 100 mM Na-pyruvate, 10 mM Hepes pH 7.2, $5\times10^{-5}$ M 2-mercapto-ethanol, 100 u/ml penicillin, 100 μg/ml streptomycin and 5 μg/ml nystatin. SEB (lot 14–30, from the Department of Toxinology, U.S. Army Medical Research Institute of Infectious Diseases), SEA or TSST-1 (Sigma) were added to 100 ng/ml.

RNase Protection Analysis

Total RNA was extracted with guanidinium isothiocyanate [Chomczynski and Sacchi, Anal Biochem 162:156 (1987)]. RNase protection analysis was done [Arad et al. (1995) ibid.] using genomic antisense RNA probes transcribed with [α-$^{32}$P]UTP in vitro from DNA inserted into pBS (Promega). The IL-2 probe (600 nucleotides (nt)), transcribed from the T7 promoter, is complementary to the third exon and a portion of the third intron of the IL-2 gene; in 8 M urea-polyacrylamide gels, it yields an RNA fragment of 117 nt protected by IL-2 mRNA. The IFN-γ probe (274 nt), transcribed from the T3 promoter, is complementary to the third exon and a portion of the third intron of the IFN-γ gene and yields an RNA fragment of 183 nt protected by IFN-γ mRNA. The TNF-β probe (700 nt), transcribed from the T3 promoter, is complementary to part of exon 1, exon 2, exon 3, and portions of intron 3 and exon 4; TNF-β mRNA protects 2 fragments of 274 and 263 nt. Sense RNA transcripts yielded no detectable signal upon hybridization. Antisense RNA probes for 18S rRNA (protecting 90 nt) or β-actin (protecting 415 nt) served as loading controls.

Quantitative Dot Blot Hybridization of IL-2 and IFN-γRNA

PBMC from 1-ml cultures were collected and lysed in 7.5 M guanidinium-HCl. RNA, precipitated overnight in ethanol at −20° C., was dissolved into formaldehyde and incubated for 15 min at 60° C. Four serial 2-fold dilutions, made in 10× saline sodium citrate, were applied in duplicate to nitrocellulose sheets, using a 96-well dot blot apparatus. After baking in a vacuum oven at 80° C., sheets were hybridized separately with $^{32}$P-labeled antisense RNA probes for human IL-2 and IFN-γ, respectively. Exposed autoradiograms were scanned at 630 nm in an ELISA reader. RNA levels are expressed in units of $A_{630}$. Serial twofold dilutions of a given RNA sample yield a linear optical density response over a 200-fold range of intensities of gene expression that is proportional to the concentration of specific RNA present in each sample [Arad et al. (1995) ibid.; Gerez et al., Clin Immunol Immunopathol 58:251 (1991); Kaempfer et al., J Clin Oncol 14:1778 (1996)].

Synthesis of SEB-related Peptides

Peptides were synthesized in the Peptide Synthesis Unit of The Hebrew University-Hadassah Medical School, Jerusalem. tBOC chemistry (tertiary butoxycarbonyl protection of amino termini) was used to prepare one batch of peptides, used for FIGS. 3–5, Table 2, and trials 2 and 3 in Table 3; peptides were cleaved, and the side chain deprotected, with fluoric acid and then solubilized with 10% dimethyl-sulfoxide. The same amount of dimethylsulfoxide was added to control cell cultures. Fluoronylmethoxycarbonyl (FMOC) chemistry was used to prepare a second batch of peptides, used for FIGS. 6 and 7 and trial 1 in Table 3; peptides were cleaved, and the side chain deprotected, with triflouroacetic acid. Triflouroacetic acid-peptide salts were soluble in culture medium. In the experiment of FIG. 6, corresponding peptides from both batches were also compared and found to have equal antagonist activity. N-terminal laurylcysteine (LC-) and C-terminal cysteine (-C) were added under the same conditions used for the other amino acids. Peptides were >95% purity by HPLC.

Proteosome or KLH Coupling of Peptides

Outer membrane proteosome preparations were stored at −70° C. after purification, as described [Mallett et al., Infect Immun 63:2382 [1995)], from group B type 2 *Neisseria meningitidis* by extraction of a paste of phenol-killed bacteria with a solution of 6% Empigen BB (Albright and Wilson, Whitehaven, Cumbria, UK) in 1 M calcium chloride, followed by precipitation with ethanol, solubilization in Tris-buffered saline with EDTA and 1% Empigen BB, reprecipitation with ammonium sulfate, and then resolubilization in the Tris buffer with 1% Empigen BB [Lowell et al. (1996) ibid.]. LC-peptides were coupled to proteosomes as described by Lowell et al. [Lowell et al. (1996) ibid.]. Maleimide-activated keyhole lympet hemocyanin (KLH) was coupled to C-terminal C residues following instructions of the supplier (Pierce).

Immunization

Rabbits were immunized intramuscularly with 100 μg of proteosome- or KLH-coupled peptides, at 0 and 3 weeks. Three bleeds were performed; data for the third bleed are shown in Table 2. BALB/c mice were immunized with 50–100 μg of proteosome- or KLH-coupled peptides, via the parenteral (intramuscular) or intranasal routes as described by Lowell et al. [Lowell et al. (1996) ibid.]. Blood was collected periodically from rabbits from the ear vein, and from mice from the retroorbital plexus at 3 weeks before challenge with SEB. SEB-specific IgG was assayed by ELISA as [Lowell et al., (1996) ibid.].

SEB Challenge Assays of Vaccine Efficacy in Vivo

Lot 14–30 SEB was used for challenge. For parenteral (IM) or intranasal (IN) challenge, D-galactosamine sensitization was used in conjunction with SEB, as described [Lowell et al. (1996)].

Example 1

Peripheral blood mononuclear cells (PBMC) are used to provide a quantitative measure of the primary response of human T cells to an exotoxin, through expression of the Th1 type cytokine genes encoding IL-2, IFN-γ, and TNF-β. Gene expression is analyzed within hours after stimulation, providing a more direct and immediate measure of the action of SEB than cell proliferation which results from a complex series of events.

Induction of IL-2, IFN-γ and TNF-β Gene Expression by SEB

Exposure of PBMC to SEB leads to induction of IL-2 and IFN-γ mRNA, shown by quantitative dot blot hybridization (FIGS 1A–1C) and RNase protection analysis with a genomic antisense RNA probe (FIG. 1D). Both methods yield similar patterns of induction, characterized by a transient wave of IL-2 mRNA and more prolonged expression of IFN-γ mRNA. TNF-β mRNA was induced more gradually (FIG. 1E). Patterns of mRNA have thus been documented to reflect the expression of the active proteins.

Example 2

Design of SEB-Related Peptides

Fourteen peptides representing particular SEB domains were synthesized (Table 1; peptides were >95% purity by HPLC) and assayed for the ability to block SEB-mediated induction of IL-2, IFN-γ or TNF-β gene expression. Identification of such a peptide could be useful for developing a peptide vaccine against SEB and more directly, for preventing the harmful effects of SEB on the immune response. Multiple, widely separated regions within SEB interact with the TCR on one hand and with the MHC class II molecule on the other [Swaminathan et al. (1992) ibid.; Jardetzky et al., Nature 368:711 (1994)]. Domains chosen consist of amino acid residues 13–33, 41–61, 81–93 and 208–218, essential for binding to TCR and MHC class II; residues 21–29 and 48–61, essential for binding to the TCR; and residues 13–17 and 44–52, essential for binding to MHC class II [Swaminathan et al. (1992) ibid.]. A 12-amino acid SEB domain, made up of residues 150–161, is thought not to be involved in binding to TCR or MHC class II but forms a central turn starting within β-strand 7 and connecting it, via short βstrand 8, to α-helix 4 (Table 1 and FIG. 2). These sequences are found in the SEB molecule, except for two variants of that domain devised by the inventors: dodecamer p12(150–161) and decamer p10(152–161) (150–161* and 152–161* in Table 1, respectively).

To allow study of their immunogenicity and ability to elicit protective immunity against SEB, many of the peptides were synthesized also with an extra lauryl-cysteine residue at their N-terminus (LC-) or with an extra cysteine residue at their C-terminus (-C), as indicated in Table 1.

Example 3

Lack of SEB Agonist Activity of SEB-derived Peptides

Figure 3:
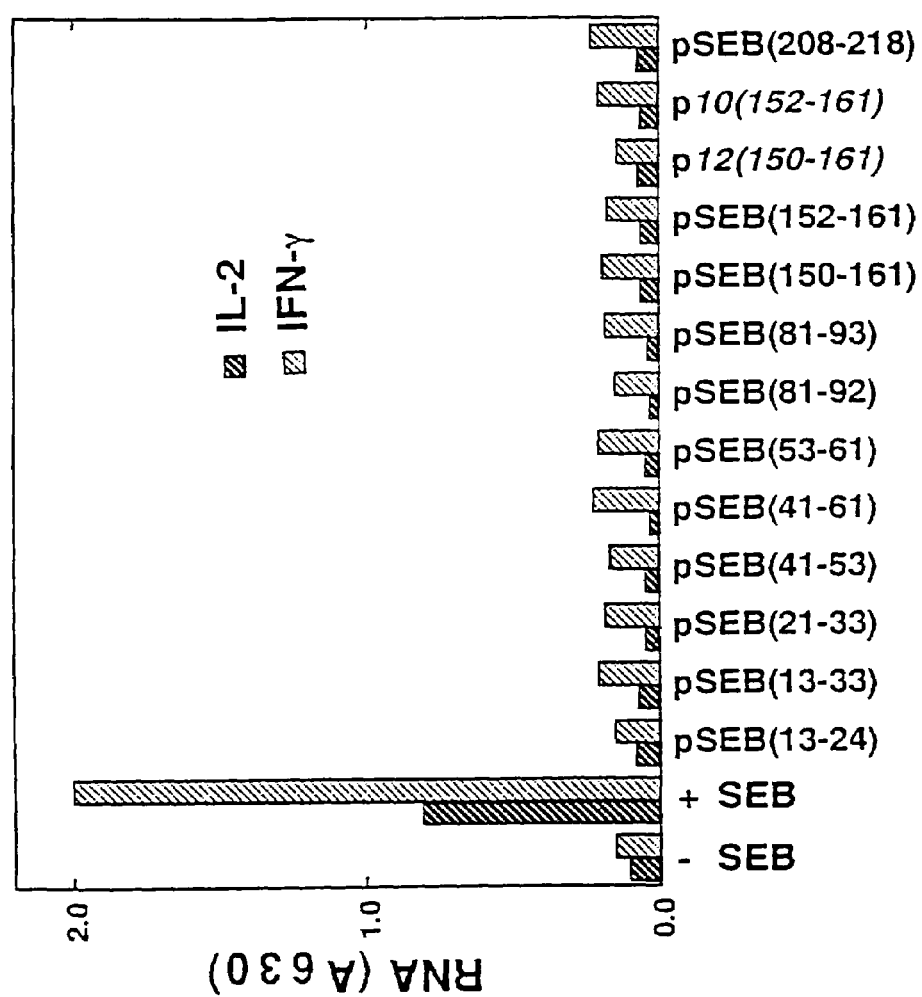

SEB agonist activity of peptides was examined by the ability to induce expression of IL-2 and IFN-γ genes. Even when present in 200-fold higher molar amounts than SEB, no peptide exhibited significant SEB agonist activity, defined as ≧2-fold increase in RNA over basal level (FIG. 3). When induction of mRNA for IL-2 (FIG. 5) or IFN-γ (not shown) was analyzed by RNase protection, pSEB(41–61), p12(150–161) and pSEB(150–161) again failed to show SEB agonist activity.

Example 4

Peptide p12(150–161) is an SEB Antagonist

Antagonist activity of SEB-related peptides was defined by the ability to block SEB-mediated induction of IL-2, IFN-γ, and/or TNF-β gene expression in PBMC. A short, unstructured peptide would be expected to compete poorly with intact SEB whose binding is stabilized by multiple interactions with the TCR and MHC class II molecule [Swaminathan et al. (1992) ibid.; Jardetzky et al. (1994) ibid.]. However, an appropriate SEB-related peptide might compete with SEB for one of its cognate sites, preventing thereby a cooperative interaction with multiple sites.

Figure 4A:
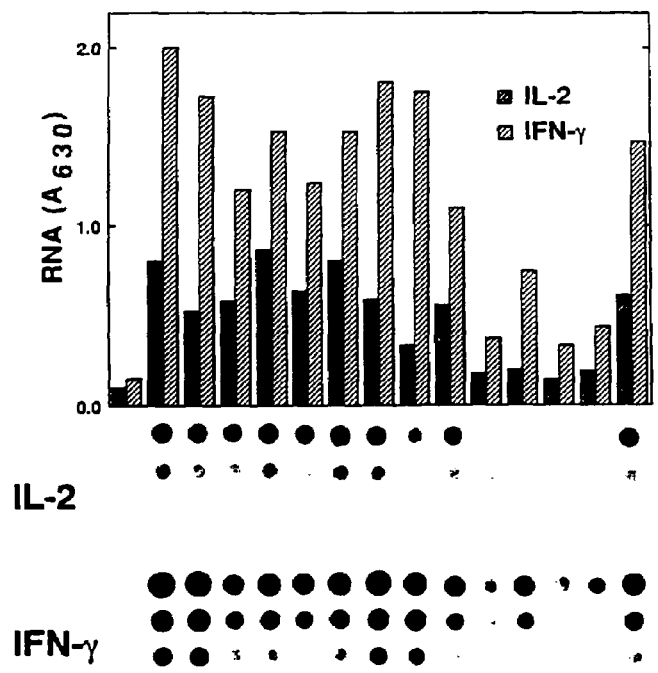
Figure 4B:
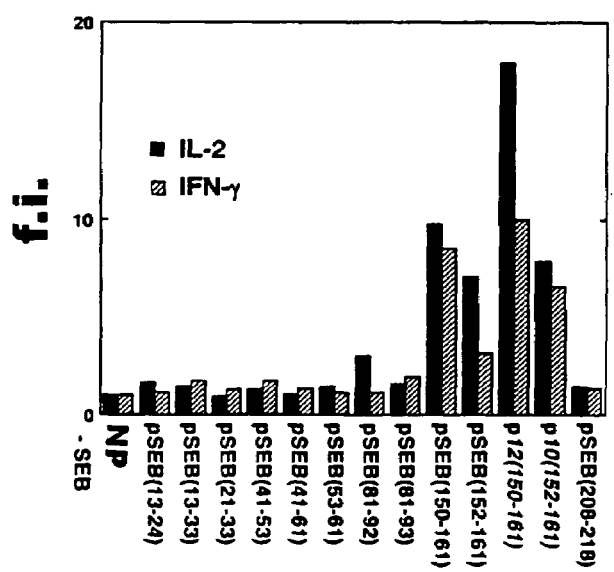

Ability to antagonize induction of IL-2 or IFN-γ gene expression was assayed by exposing PBMC populations to SEB in the presence of a 100- to 200-fold molar excess of an individual peptide. The resulting hybridization patterns for IL-2 and IFN-γ RNA are shown and quantitated in FIG. 4A. Antagonist activity is seen more clearly in FIG. 4B where extent of inhibition is plotted. Most peptides failed to inhibit SEB-mediated IL-2 mRNA induction perceptibly but pronounced antagonist activity was exhibited by peptides pSEB(150–161), pSEB(152–161), p12(150–161) and p10 (152–161). Dodecapeptide p12(150–161) (SEQ ID NO:2) stands out as antagonist, inhibiting expression of IL-2 mRNA by 18-fold and that of IFN-γ mRNA by 10-fold. Peptide p10(152–161) (SEQ ID NO:4), which lacks the 2 N-terminal amino acids of p12(150–161), showed lower, yet still significant, antagonist activity. In >5 experiments, each performed with a distinct PBMC population, SEB antagonist activity of p12(150–161) ranged from 9- to 40-fold inhibition of IL-2 gene induction. Corresponding extent of inhibition by p10(152–161) was up to 8-fold, other peptides remaining well below this value.

PBMC cultured with either pSEB(150–161) or p12 (150–161) showed undiminished viability, as judged by trypan blue exclusion analysis and recovery of total cellular RNA. The SEB antagonist activity of these peptides thus does not result from a cytotoxic effect. Both peptides reproducibly failed to inhibit PHA-mediated induction of IL-2 and IFN-γ genes (not shown).

Figure 5:
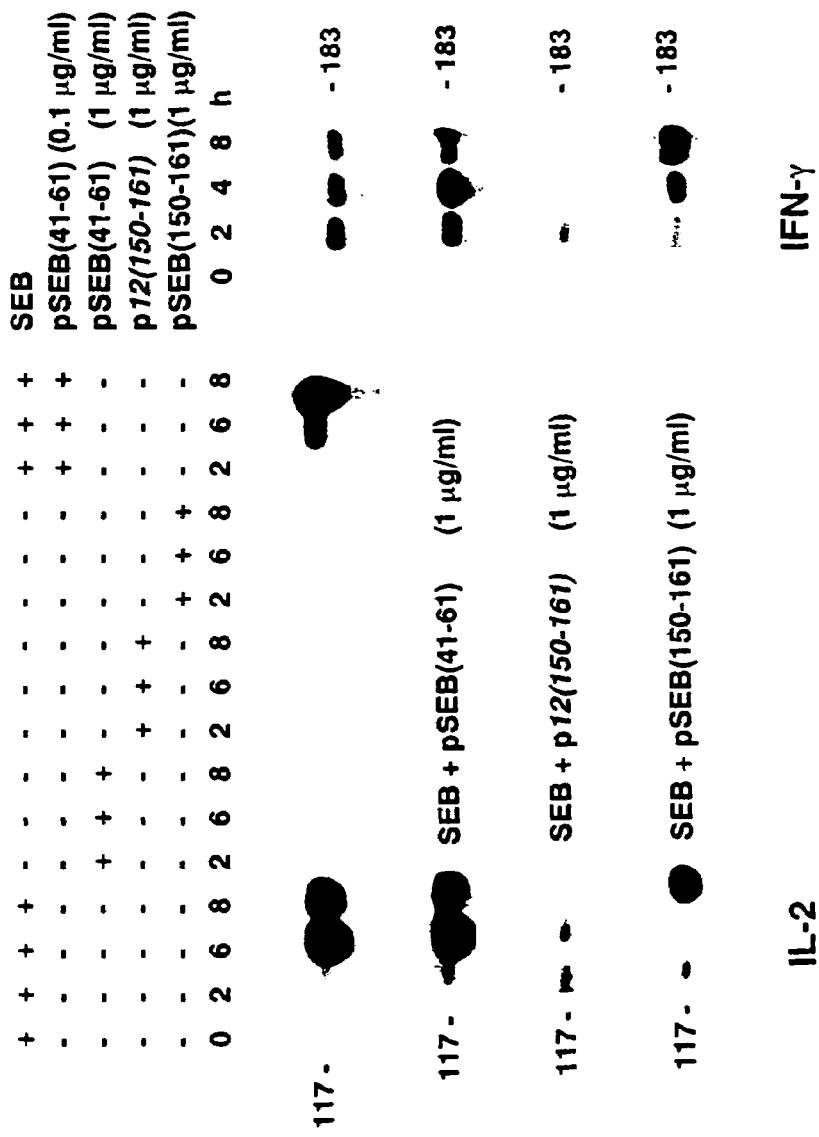

The natural homolog of p12(150–161), pSEB(150–161), was less active than the variant peptide as SEB antagonist (FIG. 4). Clear differences in antagonist activity between p12(150–161) and pSEB(150–161) are seen in FIGS. 5 and 6. Whereas pSEB(41–61), chosen as control, failed to block induction of IL-2 and IFN-γ mRNA by SEB, p12(150–161) yielded an almost complete inhibition (FIG. 5). pSEB (150–161) inhibited expression of IL-2 mRNA effectively at 6 hrs, but only partially at 8 hrs and reduced expression of IFN-γ mRNA by 2 hrs but not thereafter; a stimulatory effect seen at later times (FIG. 5) was not observed consistently (cf. FIG. 6). In the experiment of FIG. 6, p12(150–161) blocked induction of IL-2, IFN-γ and TNF-β mRNA completely, whereas pSEB(150–161) caused only partial inhibition. p12(1–161) was consistently more effective than pSEB(150–161) as SEB antagonist.

None of the peptides homologous to toxin domains involved in the interaction with T cell receptor and/or MHC class II molecule was able to inhibit the SEB-mediated induction of human IL-2, IFN-γ, and TNF-β genes. By contrast, the inventors have identified 12-mer p12 (150–161), resembling a region well removed from these active sites which has the capacity to completely block expression of these cytokine genes upon their induction by SEB. The sequence of this potent antagonist peptide is man-made, deviating at various positions from the corresponding sequence in SEE; indeed, when a peptide with the natural SEE sequence was used, pSEB(150–161), it was less effective as antagonist. Antagonist activity decreased upon removal of 2 N-terminal amino acids. Despite its high degree of conservation, the charge of the corresponding sequence in SEA is neutral whilst that of pSEB(150–161) or of p12(150–161), is positive. Indeed, although SEE is 68% homologous with SEC. it shows only 27% homology with SEA [Betley and Mekalanos, J Bacteriol 170:34 (1995)].

The region covering amino acids 150–161 overlaps partially with a larger, 31-amino acid peptide, pSEB(130–160). When conjugated to KLH, pSEB(130–160) inhibited the SEB-induced proliferation of mixed cultures of human peripheral blood monocytes and lymphocytes by 2- to 4-fold but was not unique in this property, since peptides overlapping with other SEB domains, covering amino acids 1–30, 61–92, 93–112, 151–180, 171–200 and 191–220, had a similar inhibitory effect [Jett et al. (1994) ibid.]. Although pSEB(130–160) was able to inhibit binding of SEB to human lymphocytes [Jett et al. (1994) ibid., Komisar et al., Infect Immun 62:4775 (1994)] it was shown that a smaller overlapping peptide, pSEB(150–162), failed to inhibit binding of SEB to HUT-78 cells, a human T cell line, as studied by fluorescence, whereas another peptide, pSEB(90–114), inhibited by 2-fold. Wang et al. [(1993) ibid.] showed that a synthetic peptide encoding the carboxy-terminal 41 amino acids of the superantigenic pep M5 protein of S. pyogenes inhibited pep M5-mediated T cell proliferation. They commented with respect to pSEB(152–160) that "most studies seem to indicate that this region does not contribute to mitogenicity" while emphasizing in this context that "immunologic function is not determined solely by the primary amino acid structure of a particular region but is influenced by the context in which it is located" and indicating that the longer amino acid sequence may contribute to α-helix amphi-philicity. The lack of inductive activity of pSEB (150–161) or p12(150–161) is shown in FIG. 3 for the IL-2 and IFN-γ genes and again for the IL-2 gene in FIG. 5. Indeed, the N-terminal 138 amino acids of SEB, which exclude the domain of pSEB(150–161), are sufficient for mitogenic activity [Buelow et al., J Immunol 148:1 (1992); Kappler et al., J Exp Med 175:387 (1992)]. Thus, it would be expected from these earlier studies that short peptides, especially in the region of pSEB(150–161), will not inhibit the action of SEB. Contrary to this expectation, the results of FIGS. 4–6 show that pSEB(150–161) and the non-natural p12(150–161) are powerful SEB antagonists.

Example 5

Enhancement of SEB Antagonist Activity

With PBMC populations from occasional healthy donors, it was observed that p12(150–161) was only weakly or not inhibitory to SEB. Such an experiment is illustrated in FIG. 7. Whereas p12(150–161) did not inhibit induction of IL-2 and IFN-γ mRNA, both its dimer and trimer forms were strongly inhibitory (shown for IFN-γ in FIG. 7A). FIG. 7B shows that even when diluted 100-fold, the dimer still gave a detectable inhibition.

A similar rise in efficacy was observed when p12 (150–161) was cyclized with terminal cysteines (Cys-p12 (150–161)) (FIG. 8). Given the oxidizing conditions in aqueous solution, this peptide will tend to cyclize by forming an intramolecular disulfide bridge in a zero-order reaction; multimeric forms generated by disulfide bridges between separate peptide molecules will tend to be rarer as they result from a higher order reaction. Whereas p12 (150–161) was weakly or not inhibitory at 8 hrs (FIGS. 8A and 8C), Cys-p12(150–161) showed significant SEB antagonist activity, even upon tenfold dilution (FIGS. 8B and 8D). An enhancement in SEB antagonist activity was also obtained by addition of a D-Ala residue at both N- and C-termini (see FIGS. 11 and 12 below).

Example 6

Broad-spectrum Pyrogenic Exotoxin Antagonist Activity

The SEB 150–161 domain is conserved among pyrogenic toxins. The sequence of p12(150–161), shown in SEQ ID NO: 2, differs in several positions from the corresponding sequence in SEB, <u>T</u>NKKK<u>V</u>TAQELD found in pSEB (150–161), but shared KKK and QELD motifs are spaced equally in both peptides. Residues T150, K152, E159 and D161 of this SEB domain are conserved among all staphylococcal enterotoxins [Swaminathan et al. (1992) ibid.]. Indeed, domain 150–161 of SEB is highly conserved among pyrogenic toxins, with 10/12 identities for SEA, SEC1, SEC2, and SPE A and 9/12 for SEE [Bohach and Schlievert (1987) ibid.; Couch et al. (1988) ibid.; Bohach and Schlievert (1989) ibid.]. All of these toxins contain the residues underlined above [Swaminathan et al. (1992) ibid.; Bohach and Schlievert (1987) ibid.; Couch et al. (1988) ibid.; Bohach and Schlievert (1989) ibid.].

Figure 10:
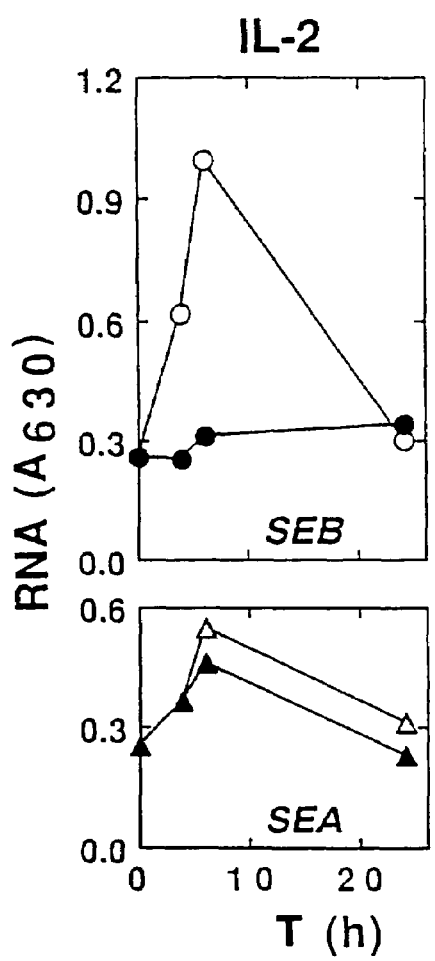

The prediction that SEB antagonist peptides may have wider antagonist activity was tested. FIG. 9 shows that pSEB(150–161) failed to inhibit the induction of IL-2 mRNA by TSST-1, although it strongly reduced the induction of this mRNA by SEB. As seen in FIG. 10, moreover, p12(150–161) effectively inhibited the induction by SEB of waves of IL-2 mRNA (A) and IFN-γ mRNA (B) but had no significant effect on their induction by SEA.

The results of FIGS. 9 and 10 lend support to the earlier conclusion that the antagonist activity of pSEB(150–161) and p12(150–161) for SEB does not result from a cytotoxic effect on the cells examined because these peptides fail to inhibit induction by TSST-1 and SEA.

These results would lead a man of the art to the conclusion that the SEB antagonist activity of the peptides examined does not extend to two less related toxins, TSST-1 and SEA.

Nevertheless, in contrast to the results of FIGS. 9 and 10 which suggest narrow specificity for the antagonist peptides, FIGS. 11 and 12 show that broad-spectrum antagonist activity is exhibited by derivatives of p12(150–161), the dimer described in FIG. 7 and p12(150–161) carrying D-Ala at both N- and C-termini.

FIG. 11 shows induction of IL-2 and IFN-γ mRNA in a PBMC population where peptide p12(150–161) did not significantly inhibit SEB-induced gene expression. However, both dimer and p12(150–161) carrying D-Ala at both N- and C-termini were effective as antagonist, with the latter showing highest antagonist activity. Despite the low homology between corresponding regions in SEB and TSST-1 (FIG. 12A), the D-Ala form also inhibited induction of IL-2 mRNA by TSST-1 (6-hour point in FIG. 11).

FIG. 12A shows, for another PBMC population, induction of IL-2 mRNA by SEB, by TSST-1 as well as by SEA. Induction of IL-2 mRNA by all three toxins was inhibited by p12(150–161) carrying D-Ala at both N- and C-termini. For SEB and TSST-1, data with the dimer of p12(150–161) are also shown. Induction of IL-2 mRNA by both toxins was inhibited by the dimer.

Induction of IL-2 mRNA by SPE A for another PMBC population is depicted in FIG. 12B. Induction of IL-2 mRNA was inhibited by p12(150–161) carrying D-Ala at both N- and C-termini.

The results of FIGS. 12A–12B show that the SEB antagonist activity of the p12(150–161) dimer and/or D-Ala forms extends to other members of the pyrogenic exotoxin family, TSST-1, SEA and the streptococcal SPE A, indicating their potential broad-spectrum toxin antagonist activity. The dimer, Cys and D-Ala forms are each more powerful as antagonist than p12(150–161) (FIGS. 7, 8 and 10). Independent of the basis for enhanced antagonist activity in p12(150–161) derivatives (they may be more stable, exhibit higher affinity for a target, or both), these results show that the sequence of p12(150–161) has the potential of being a broad-spectrum pyrogenic exotoxin antagonist.

Example 7

Dodecamer antagonist peptide p12(150–161) elicits, in rabbits, antibodies that protect human T cells, capable of expressing IL-2 and IFN-γ genes, from activation not only by SEB but also by SEA and TSST-1. This finding indicates that used as vaccine, the peptide has the potential to confer broad-spectrum protective immunity.

Antiserum Against p12(150–161) Blocks the Action of SEB, SEA, SPE A and TSST-1

Antibodies raised against a SEB-related peptide might bind to a pyrogenic exotoxin, for example SEB and modulate its action. To allow study of their immunogenicity and ability to elicit protective immunity against pyrogenic exotoxins, most peptides were synthesized also with an added N-terminal lauryl-Cys or C-terminal Cys (Table 1), to permit their linkage to proteosomes or KLH adjuvant, respectively [as described by Lowell et al. (1996) ibid.], in order to facilitate generation of antibodies. In addition, alum may be used as an immunization adjuvant directly with non-linked peptide, or after linking a peptide to proteosomes or to KLH [Lowell et al. (1996) ibid.].

Sera from rabbits immunized with individual peptides were titrated for their ability to bind SEB. Most of the peptides in Table 1 proved immunogenic by this parameter but greatly differed in titer of serum anti-SEB IgG achieved. Thus, serum against pSEB(13–33)C had a titer of 102,400 while corresponding titers for pSEB(81–93), pSEBLC (41–61) and p12LC(150–161) were 50, 1,600 and 1,600, respectively (Table 2). On the basis of the results in Table 2, one would not select p12(150–161) for use as a peptide vaccine but instead, prefer to use pSEB(13–33)C.

None of the antisera raised against individual SEB-related peptides had any SEB agonist activity, defined by ability to induce IL-2 or IFN-γ mRNA (not shown). Ability to inhibit SEB-mediated induction of these genes is examined in FIG. 13. Normal rabbit serum did not affect this induction (not shown). Consistent with its high titer of anti-SEB IgG, anti-pSEB(13–33)C serum partially inhibited induction of IL-2 and IFN-γ mRNA. However, despite its far lower titer, anti-p12LC(150–161) serum completely blocked the induction of both genes (FIGS. 13A and 13B).

Antisera against pSEB(81–93) and pSEBLC(41–61), which had low titers of anti-SEB IgG, not only failed to inhibit expression of IL-2 and IFN-γ mRNA but significantly stimulated their SEB-mediated induction (FIGS. 13A and 13B). This result was unexpected. This finding raises the possibility that elicitation of SEB-sensitizing antibodies, for example, by a toxoid [Lowell et al., Infect Immun 64:1706 (1996a); Lowell et al., Infect Immun 64: 4686 (1996b)] or mutant toxin vaccine [Stiles et al., Infect. Immun. 63:1229 (1995); Woody et al., Vaccine 15:133 (1997)], could lead, in a polyclonal antibody reaction, to exacerbation of toxic immune responses in SEB-exposed individuals. Antibodies raised against peptide p12(150–161), on the other hand, are free of exacerbating properties as measured in vitro, indicating that the peptide, or its derivatives, may serve as safer anti-toxin vaccine.

There was a striking lack of correlation between the ability of anti-peptide sera to bind SEB and to block SEB action. Antisera against pSEBLC(41–61) and p12LC (150–161) showed identical anti-SEB IgG titers yet affected induction of IL-2 and IFN-γ genes by SEB in an opposite manner, stimulation vs. complete inhibition. Apparently, certain antibodies effectively potentiate SEB action while others block it. As judged by serial dilution, inhibition of SEB-mediated gene induction was also up to 30-fold more sensitive for detecting blocking antibodies than binding of IgG to SEB.

In an earlier study, rabbit sera raised against SEB peptides 113–144, 130–160, 151–180 and 171–200 each reduced SEB-induced lymphocyte proliferation weakly (≦2.5-fold), apparently in a nonspecific manner [Jett et al. (1994) ibid.].

Antibodies against p12(150–161) have broad-spectrum toxin blocking activity. In FIGS. 14A and 14B, SEA was used as inducer. Again, sera raised against p12LC(150–161) and pSEB(13–33)C strongly inhibited IL-2 and IFN-γ gene expression. As for SEB (FIG. 13A), sera raised against pSEB(81–93) or pSEBLC(41–61) failed to inhibit but instead, stimulated induction of IL-2 mRNA by up to 7-fold over the SEA control. Antiserum against pSEB(81–93) also stimulated expression of IFN-γ mRNA.

Antibodies raised against p12(150–161) and pSEB (21–33)C likewise inhibited the action of the even less related toxin, TSST-1 (FIG. 15A). Furthermore, antibodies raised against p12(150–161) inhibited the action of the streptococcal toxin, SPE A (FIG. 15B).

Hence, as judged from inhibition of IL-2 and/or IFN-γ gene expression analysis, protective activity of antibodies elicited by p12(150–161) is not narrowly restricted in range of pyrogenic exotoxins (FIGS. 13–15). These results suggest that p12(150–161) is potentially a broad-spectrum peptide vaccine against pyrogenic exotoxins.

Example 8

Protective Effect of SEB-related Peptides as SEB Vaccine in Mice

The finding that antiserum against p12(150–161) blocks the action of SEB in human PBMC suggested its potential as peptide vaccine. To examine this point, the D-galactosamine-treated mouse model was used [Lowell et al. (1996a) ibid.]. Mice were repeatedly immunized with individual peptides and then challenged with a lethal dose of SEB. Table 3 details the results of 3 separate trials.

In the first, formalin-inactivated intact SEB toxoid protected 20% of the mice against a lethal dose of SEB, either upon parenteral (i.m.) or intranasal vaccination. The fact that SEB toxoid did not afford complete protection as reported [Lowell et al. (1996a) ibid.] shows that the conditions of toxin challenge were more severe in the present experiment. In this trial, proteosome-coupled p12(150–161) yielded 10% protection. Relative to SEB toxoid, p12(150–161) thus did show protective activity.

In the second trial, the ability of proteosome-coupled pSEB(150–161) and p12(150–161) to provide immune protection against SEB challenge was compared to that of several larger, synthetic peptides [Jett et al. (1994)] derived from the SEB amino acid sequence, including pSEB (130–160) which overlaps almost completely with pSEB (150–161) and p12(150–161). None of the larger peptides showed detectable protective activity against intranasal challenge with SEB, yet both pSEB(150–161) and p12 (150–161) afforded protection, evident from 22–29% survival (Table 3). pSEB(150–161) also elicited protective immunity (22%) when vaccination was by the intramuscular route (trial 3) rather than intranasally (trial 2). By contrast, two larger peptides, pSEB(130–160) and pSEB(151–180) that overlap in part with pSEB(150–161), failed to give protection. Peptide pSEB(13–33)C, moreover, though able to elicit in rabbits a high titer of IgG that inhibit the action of SEB, SEA and TSST-1 on human T cells, capable of expressing IL-2 and IFN-γ genes, in vitro (Table 2 and FIGS. 13–15), was not protective in mice.

Despite the severity of challenge with SEB toxin in these early trials, two SEB-related peptides exhibiting SEB antagonist activity, pSEB(150–161) and p12(150–161), also showed activity as SEB vaccine. Protective effect of SEB-related peptides tended to correlate with SEB antagonist activity on human PBMC in vitro (FIGS. 4–6) rather than with the ability to elicit SEB-binding IgG (Table 2). In trials 2 and 3, murine SEB-binding IgG titers were 50–200 for all peptides and did not correlate with protection (Table 3). Significantly, peptide pSEB(13–33)C, though able to elicit in rabbits a high titer of IgG that bind SEB and inhibit SEB action on PBMC in vitro (Table 2 and FIG. 13, was neither active as SEB antagonist (FIG. 4) nor protective in mice (Trial 3).

These examples show that it is possible to design an effective pyrogenic exotoxin antagonist. It is surprising that a linear, unstructured dodecapeptide, such as p12(150–161) or pSEB(150–161), can compete effectively with the intact, folded 239-amino acid SEB protein chain which interacts at multiple domains with regions in the MHC Class II molecule and in the T cell receptor. Such concerted interaction would lead to far higher affinity of binding for intact SEB vis-a-vis the peptides. Yet, as shown clearly in FIGS. 4–6, the action of SEB on human PBMC can be neutralized almost completely by the dodecapeptides, especially by p12(150–161). This first-generation antagonist, moreover, elicited in rabbits the production of antibodies that block the action of SEB on human T cells.

Subtle changes in peptide composition had marked effects on its SEB antagonist activity (FIGS. 4–6), indicating that substantial improvement is possible by methods known to a man of the art. In principle, significantly enhanced pyrogenic exotoxin antagonist activity can be obtained by generating dimers or multimeric forms (as shown in FIG. 7) or by constraining conformation, by use of disulfide bridges (as shown in FIG. 8), by internal bridges, short-range cyclizations or other means. In principle, improvement of the stability of the described peptides by these means will also render them more effective as peptide vaccine against pyrogenic toxins.

For example, the amino acid sequence of these dodecapeptides could also be extended stepwise at their N- or C-termini, or both, either with the natural SEB amino acid sequence, or with a D-amino acid that will tend to render the peptide less amenable to digestion by L-amino-acid-specific proteases (as shown for D-Ala in FIGS. 11 and 12) or with aromatic residues such as Trp to enhance the hydrophobicity of the resulting peptide, or with a random sequence of amino acids followed by selection using existing methods, for example, phage display, in order to obtain peptide(s) with enhanced antagonist activity and/or immunoprotective properties. Immunogenicity may be enhanced, for example, by use of in vitro reconstituted MHC/peptide complex as described by Sakita et al., [Sakita et al., J. Immunol. Methods 192:105 (1996)].

There are few examples of short peptides able to bind with sufficiently high affinity to a receptor in order to mimic the binding of the full-length ligand or to block its action. A T-cell receptor antagonist peptide of 4 amino acids was able to inhibit clinical disease progression in experimental allergic encephalomyelitis mediated by a diverse T cell repertoire [Kuchroo et al., J. Immunol. 153:3326 (1994)]. Peptides derived from the predicted helical region of MHC class II molecules may interact directly with T cell receptors: one such a peptide, a 16-mer, appeared capable of modulating immune responses in a physiologically significant manner [Williams et al., Immunol Res 11:11, (1992)]. In another example, a synthetic, 22-amino-acid segment of the human IFN-γ receptor was found to antagonize the action of IFN-γ [Seelig et al., J Biol Chem 270:9241 (1995)]. The linear forms of peptides generally lack a stable conformation in solution. Interaction with the cognate binding site on a receptor may induce folding of the peptide to mimic conformation in the native protein. Significant improvement in binding affinity can be achieved by generating dimers or multimeric forms of the peptide (FIG. 7) or by constraining conformation, for example, through cyclization (FIG. 8). Thus, by dimerizing bioactive peptides based on an antibody hypervariable region sequence, higher affinity binding was produced; an optimized cyclic peptide showed up to 40-fold enhanced affinity when compared to the linear form [Williams et al., J Biol Chem 266:5182, (1991)]. A hexapeptide, once cyclized by oxidizing a Cys-hexapeptide-Cys form, showed a higher avidity for the collagen receptor than the more flexible linear structure [Cardarelli et al., J Biol Chem 267:23159 (1992)]. A synthetic 15-amino-acid peptide mimic of plasma apolipoprotein E failed to bind to the low density lipoprotein receptor but its dimeric form was active in binding; a trimer, moreover, had 20-fold greater activity than the dimer [Dyer and Curtiss, J Biol Chem 266:22803 (1991)]. In addition to affecting peptide conformation and thus enhancing its binding affinity and/or immunogenicity, multimerization or cyclization of a peptide may also enhance its biostability, thus enhancing its efficacy as vaccine. These examples provide to a man of the art methods to improve upon the antagonist activity of SEB-related peptides as detailed in this invention and through this criterion, potential vaccine efficacy.

Methods for generating multimeric or cyclic forms of peptides exist, as by direct synthesis (FIG. 7). Another approach is to generate two terminal Cys residues as described above [Cardarelli et al., (1992) ibid.]; their oxidation will yield both cyclic and multimeric forms, mostly dimers (FIG. 8). An efficient procedure for the preparation of protected cyclized and protected symmetrical dimeric peptide disulfides by oxidative detachment from a support has been described [Rietman et al., Int J Pept Protein Res 44:199 (1994)]. Fully cyclic forms of peptides will lack free termini but cyclic peptides can be made by internal bridges, or short-range cyclizations [Toniolo, Int J Peptide Protein Res 35:287 (1990); Gilon et al., Biopolymers 31:745 (1991)] to allow synthesis of LC- or -C termini.

The experimental approach employed here used expression of human cytokine genes in vitro as a tool for designing both a broad-spectrum pyrogenic toxin antagonist and a prototypical peptide vaccine. This molecular approach is far more rapid than conventional methods that are based solely on animal tests, allowing evaluation of the biological properties of a candidate peptide well before moving on to animal studies for analysis of vaccine efficacy, prophylactic and therapeutic activity. Specifically, analysis of pyrogenic toxin antagonist activity on human T cells can be used to direct effective vaccine development, even before ability to elicit antibodies is studied in animals.

Efficacy of potential vaccine candidates can be evaluated not only by their pyrogenic toxin antagonist activity but also by their ability to elicit production of antibodies in rabbits (shown for SEB in Table 2) that can block the harmful action of pyrogenic exotoxins on human lymphoid cells (FIGS. 13–15), independently of their ability to bind toxin. The examples show that assay of the ability of anti-peptide antibodies to block the action of SEB on human cytokine gene expression is far more sensitive than assay of the ability to bind SEB (Table 2 and FIGS. 13 and 14. At least certain antisera showing very high anti-SEB IgG titers (Table 2) are not necessarily protective against the toxin. This result casts doubt on the relevance of IgG assays for evaluating or predicting immunoprotection against SEB, as also shown in Table 3, trials 2 and 3.

In order to vaccinate humans effectively against one or more pyrogenic toxins, there is a need to assess the efficacy of vaccination. This requirement is independent of the nature of the vaccine, whether a toxoid, a mutant toxin or a peptide. However, unlike experimental animals (Table 3), humans cannot be challenged with toxin to test if the vaccination was effective. Therefore, it is desirable to use a surrogate marker instead, preferably one based on human T cell activation. Such a marker is provided through the method used in FIGS. 13–15, which measures the ability of serum from an immunized individual to antagonize toxin-mediated activation of human T cells. Given the fact that humans are far more sensitive than mice to staphylococcal toxins, use of human T cells as shown in FIGS. 13 to 15 has advantages over use of murine cells [Stiles et al., Infect Immun 63:1229 (1995)]. Toxin-mediated activation of T cells is preferably measured by the induction of IL-2, IFN-γ or TNF-β gene expression, which yields information on the response of these genes within a few hours after their induction, long before any effect on cell proliferation.

SEB-related peptides with demonstrated SEB antagonist activity, p12(150–161) and pSEB(150–161), carry sequence elements that are highly conserved amongst pyrogenic toxins. Through improved peptide design, including introduction of structural constraints, peptides may thus be generated that exhibit broader antagonist activity (FIGS. 11, 12). A peptide antagonist able to protect against a range of related enterotoxins would be far more valuable than a narrowly active one.

Rabbit sera raised against p12(150–161) were equally able to block the ability of SEB, SEA, SPE A or TSST-1 to induce expression of IL-2 and IFN-γ genes (FIGS. 13–15) These results show a potential for broader protective immunity. A peptide vaccine able to impart protective immunity against a range of related enterotoxins would be far more valuable than a narrowly active one.

An unexpected finding, shown in FIGS. 13 and 14, is that antisera against certain SEB peptides not only fail to block the action of SEB on human lymphoid cells, but actually stimulate it significantly. This result should alert one to the possibility that vaccination with such peptide domains, including those present in SEB toxoid or other derivatives of the SEB toxin molecule, could sensitize an exposed person to the lethal effects of SEB and other pyrogenic exotoxins, for example SEA, rather than protect him.

TABLE 1

SEB-related peptides prepared for this study

| Position | Amino acid sequence | LC- | -C |
|---|---|---|---|
| 13–24 | K S S K F T G L M E N M | + | – |
| 13–33 | K S S K F T G L M E N M K V L Y D D N H V | + | + |
| 21–33 | M E N M K V L Y D D N H V | + | + |
| 41–53 | I D Q F L Y F D L I Y S I | – | – |
| 41–61 | I D Q F L Y F D L I Y S I K D T K L G N Y | + | + |
| 51–61@ | Y S I K D T K L G N Y | – | + |
| 53–61 | I K D T K L G N Y | + | – |
| 81–92 | Y V D V F G A N Y Y Y Q | + | – |
| 81–93 | Y V D V F G A N Y Y Y Q C | – | – |
| 150–161 | T N K K K V T A Q E L D | + | – |
| 150–161* | Y N K K K A T V Q E L D | + | – |
| 152–161 | K K K V T A Q E L D | – | – |
| 152–161* | K K K A T V Q E L D | – | – |
| 208–218 | F D Q S K Y L M M Y N | + | + |

LC- Lauryl-cysteyl residue added at N-terminus
-C Cysteyl residue added at C-terminus
@Only the -C form was studied
*Variant of the naturSEB sequence

TABLE 2

Anti-SEB antibody titers
in sera from rabbits immunized with SEB-related peptides

| SEB Peptide | SEB IgG Titer |
|---|---|
| pSEBLC(13–24) | 800 |
| pSEBLC(13–33) | 800 |
| pSEBLC(21–33) | 100 |
| pSEBLC(41–61) | 1,600 |
| pSEBLC(53–61) | 1,600 |
| pSEBLC(81–92) | 1,600 |
| p12LC(150–161) | 1,600 |
| pSEBLC(208–218) | 1,600 |
| pSEB(13–33)C | 102,400 |
| pSEB(21–33)C | 25,600 |
| pSEB(41–61)C | 200 |
| pSEB(51–61)C | 400 |

TABLE 2-continued

Anti-SEB antibody titers in sera from rabbits immunized with SEB-related peptides

| SEB Peptide | SEB IgG Titer |
|---|---|
| pSEB(81–93) | 50 |
| pSEB(208–218)C | 200 |

See Table 1 for explanation of SEB peptides. For immunization, peptides carrying LC at their N-terminus were coupled to proteosomes; peptides carrying C at their C-terminus were coupled to KLH. Sera were assayed for IgG able to bind SEB.

TABLE 3

Protective Effect of SEB Peptides in Mice

| Trial | Vaccine | No. of Animals | Vaccine Route | Challenge Route | Challenge (µg SEB) | IgG Titer | Percent Survival |
|---|---|---|---|---|---|---|---|
| 1 | p12LC(150–161) | 10 | IM | IM | 25 | | 10 |
|   | p12LC(150–161) | 10 | IN | IM | 25 | | 10 |
|   | SEB Toxoid | 10 | IM | IM | 25 | | 20 |
|   | SEB Toxoid | 10 | IN | IM | 25 | | 20 |
| 2 | pSEBLC(150–161) | 7 | IN | IN | 350 | 200 | 29 |
|   | p12LC(150–161) | 9 | IN | IN | 350 | 200 | 22 |
|   | pSEBLC(93–112) | 9 | IN | IN | 350 | 200 | 0 |
|   | pSEBLC(130–160) | 9 | IN | IN | 350 | 200 | 0 |
|   | pSEBLC(191–220) | 9 | IN | IN | 350 | 200 | 0 |
|   | pSEB(191–220)C | 9 | IN | IN | 350 | 50 | 0 |
|   | Control | 5 | IN | IN | 350 | 100 | 0 |
| 3 | pSEBLC(150–161) | 9 | IM | IN | 350 | 200 | 22 |
|   | pSEB(13–33)C | 9 | IM | IN | 350 | 100 | 0 |
|   | pSEBLC(93–112) | 9 | IM | IN | 350 | 200 | 0 |
|   | pSEBLC(130–160) | 9 | IM | IN | 350 | 100 | 0 |
|   | pSEBLC(151–180) | 9 | IM | IN | 350 | 200 | 0 |
|   | pSEBLC(191–220) | 9 | IM | IN | 350 | 200 | 0 |
|   | pSEB(191–220)C | 9 | IM | IN | 350 | 50 | 0 |

Groups of mice were vaccinated with SEB-related peptides or SEB toxoid as indicated. SEB toxoid [Lowell et al., (1996) ibid.], peptides pSEB(93–112), pSEB(130–160), pSEB(151–180), pSEB(191–220) and pSEB(191–220)C [Jett et al., (1994) ibid.] and preparation of LC-derivatives for coupling to proteosomes [Lowell et al., (1996) ibid.], were described elsewhere. In trial 1, 2 vaccinations were given 2 weeks apart, with SEB challenge after 1 month. In trials 2 and 3, 3 vaccinations were given at 2-week intervals, followed by a boost after 6 weeks and SEB challenge 2 weeks later. IgG were determined 3 weeks before challenge. IM, intramuscular; IN, intranasal.

Table 4 lists for each of the SEQ ID NOs' of the sequence listing, the corresponding alternative notation used in the specification.

TABLE 4

Identification of SEB related peptides by their SEQ ID Numbers

| SEQ ID NO: | Alternative notation | Sequence |
|---|---|---|
| SEQ ID No. 1 | pSEB(150–161) | T N K K K V T A Q E L D |
| SEQ ID No. 2 | p12(150–161) | Y N K K K A T V Q E L D |
| SEQ ID No. 3 | pSEB(152–161) | K K K A T V Q E L D |
| SEQ ID No. 4 | p10(152–161) | K K K V T A Q E L D |
| SEQ ID No. 5 | pSEBLC(150–161) | lc T N K K K V T A Q E L D |
| SEQ ID No. 6 | p12LC(150–161) | lcY N K K K A T V Q E L D |
| SEQ ID No. 7 | Dimer | Y N K K K A T V Q E L D Y N K K K A T V Q E L D |
| SEQ ID No. 8 | Trimer | Y N K K K A T V Q E L D Y N K K K A T V Q E L D Y N K K K A T V Q E L D |
| SEQ ID No. 9 | Cys-p12(150–161) | C Y N K K K A T V Q E L D C |
| SEQ ID No. 10 | D-Ala | daY N K K K A T V Q E L Dda |
| SEQ ID No. 11 | Ac-p12(150–161) | acY N K K K A T V Q E L Dda |
| SEQ ID No. 12 | SEB | E S Q P D P K P D E L H K S S K F T G L M E N M K V L Y D D N H V S A I N V K S I D Q F L Y F D L I Y S I K D T K L G N Y D N V R V E F K N K D L A D K Y K D K Y V D V F G A N Y Y Y Q C Y F S K K T N D I N S H E T D K R K T C M Y G G V T E H N G N Q L D K Y R S I T V R V F E D G K N L L S F D V Q T N K K K V T A Q E L D Y L T R H Y L V K N K K L Y E F N N S P Y E T G Y I K F I E N E N S F W Y D M M P A P G D K F D Q S K Y L M M Y N D N K M V D S K D V K I E V Y L T T K K K | lc, N-lauryl-cysteyl; da, D-Ala; ac, N-acetyl.

Example 9

Inhibition of Action of SEB and TSST-1 on Human Peripheral Blood Mononuclear Cells by p12(150–161) Carrying a D-Ala Residue at Both N- and C-termini (i) Groups of 10 mice each (9–10 week BALB/C females) were injected intraperitoneally with 20 mg per mouse of D-galactosamine. Two hours later, one group received 5 µg per mouse of p12(150–161) carrying a D-Ala residue at both N- and C-termini, by intravenous injection. Thirty minutes later, each mouse received 20 µg of SEB by intraperitoneal administration. Survival in each group was determined thereafter, at the times in hours indicated in FIG. 16. Surviving animals showed no signs of malaise and were indistinguishable from normal controls in behavior; they survived for as long as monitored, two weeks.

(ii) Groups of 10 mice each (9–10 week BALB/C females) were injected intraperitoneally with 20 mg per mouse of D-galactosamine. Two hours later, 25 µg per mouse of p12(150–161) carrying a D-Ala residue at both N- and C-termini were administered to one group by intravenous injection and to a second group by intraperitoneal administration. Control group mice did not receive peptide. Thirty minutes later, each mouse received 20 µg of SEB by intraperitoneal administration. Survival in each group was determined thereafter, at the times in hours indicated in FIG. 17. Surviving animals showed no signs of malaise and were indistinguishable from normal controls in behavior; they survived for as long as monitored, two weeks.

(iii) Groups of 10 mice each (9–10 week BALB/C females) were injected intraperitoneally with 40 mg per mouse of D-galactosamine. Two hours later, 25 µg per mouse of p12(150–161) carrying a D-Ala residue at both N- and C-termini were administered by intravenous injection to each group except a control group of 20 mice. Thirty minutes later, each mouse received 5 µg of TSST-1 by intraperitoneal administration. An additional intravenous injection of 25 µg per mouse of the peptide were administered at 3 hr post-challenge or at 3 and 18 hr post-challenge. Survival in each group was determined thereafter, at the times in hours indicated in FIG. 19. Surviving animals showed no signs of malaise and were indistinguishable from normal controls in behavior; they survived for as long as monitored, two weeks.

While 100% of mice exposed to SEB lethal challenge died within 1–2 days in the control group, 100% survived lethal challenge with SEB when p12(150–161) carrying a D-Ala residue at both N- and C-termini was administered intravenously half an hour before challenge, and 70% when it was administered intraperitoneally (FIGS. 16–18). Surviving animals showed no signs of malaise and were indistinguishable from normal controls in behavior; they survived for as long as monitored, two weeks. No side effects of p12(150–161) carrying a D-Ala residue at both N- and C-termini could be detected.

To extend this result to other toxins and to demonstrate broad-spectrum protective activity of this peptide, lethal challenge with TSST-1 was tested. Within the superantigen toxin family, TSST-1 is most remote from SEB, showing only 6% amino acid homology for the whole toxin molecule. TSST-1 kills more slowly than SEB, requiring a longer toxin exposure (FIGS. 17 and 19). p12(150–161) carrying a D-Ala residue at both N- and C-termini did not protect against lethal challenge with TSST-1 when administered once, just before challenge, but it afforded significant protection upon repeated administration post-challenge (FIG. 19). The protective effect of p12(150–161) carrying a D-Ala residue at both N- and C-termini became more pronounced with increasing number of administrations (FIG. 19), showing that survival from TSST-1 challenge is dependent on sustained presence of the peptide.

The p12(150–151) peptide carrying D-Ala residues at both its N- and C-termini, which is SEB-related, afforded good antagonist activity not only against SEB intoxication, but also against the remotely homologous TSST-1. Thus, p12(150–151) peptide carrying D-Ala residues at both its N- and C-termini can be used as an effective broad-spectrum antagonist against pyrogenic exotoxins.

The invention claimed is:

1. An isolated and purified peptide consisting of:
   a) a peptide consisting of an amino acid sequence which is within a domain of a pyrogenic exotoxin which domain forms a central turn in the exotoxin and includes β-strand 7, short β-strand 8, and α-helix 4, based on the domain numbering of *Staphylococcus aureus* enterotoxin B (SEB), said sequence starting within or immediately after β-strand 7 and ending within α-helix 4, wherein said isolated peptide does not have toxin agonist activity and is capable of antagonizing toxin-mediated activation of T-lymphocytes;
   b) a peptide of a) having insertions, deletions or substitutions of up to three amino acids, wherein the resultant peptide does not have toxin agonist activity and is capable of antagonizing toxin mediated activation of T-lymphocytes;
   c) a peptide of a) or b) that is extended at the N-terminus and/or the C-terminus by one or two naturally occurring or synthetic amino acid residues, or by an organic moiety that is not a naturally-occurring or synthetic amino acid residue, wherein the resultant peptide does not have toxin agonist activity and is capable of antagonizing toxin mediated activation of T-lymphocytes;
   d) a dimer or multimer of a), b), or c), wherein the resultant peptide does not have toxin agonist activity and is capable of antagonizing toxin mediated activation of T-lymphocytes; or
   e) a peptide of a), b) or c) in a constrained conformation, wherein the resultant peptide does not have toxin agonist activity and is capable of antagonizing toxin mediated activation of T-lymphocytes.

2. A peptide in accordance with claim 1, wherein said peptide of a) consists of a dodecamer that is part of said domain consisting of amino acids 150–161, using the amino acid number of SEB.

3. An isolated and purified peptide consisting of:
   a) a peptide of the amino acid sequence Lys Lys Xaa Xaa Xaa Xaa Gln Glu Leu Asp (SEQ. ID NO.:13, Xaa Xaa Lys Lys Xaa Xaa Xaa Xaa Gln Glu Leu Asp (SEQ. ID NO.:14) or
      (Thr or Tyr) Xaa Lys Xaa Xaa Xaa Xaa Xaa Xaa Glu Xaa Asp (SEQ. ID NO.:15),
   wherein said peptide does not have toxin agonist activity and is capable of antagonizing toxin mediated activation of T-lymphocytes;
   b) a peptide of a) that is extended at the N-terminus and/or the C-terminus by one or two naturally occurring or synthetic amino acid residues, or by an organic moiety that is not a naturally-occurring or synthetic amino acid residue, wherein the resultant peptide does not have toxin agonist activity and is capable of antagonizing toxin mediated activation of T-lymphocytes;
   c) a dimer or multimer of a), or b), wherein the resultant peptide does not have toxin agonist activity and is capable of antagonizing toxin mediated activation of T-lymphocytes; or
   d) a peptide of a), or b) in a constrained conformation, wherein the resultant peptide does not have toxin agonist activity and is capable of antagonizing toxin mediated activation of T-lymphocytes.

4. A peptide in accordance with claim 3, wherein said peptide of a) is SEQ. ID NO.:13.

5. A peptide in accordance with claim 3, wherein said peptide of a) is SEQ. ID NO.:14.

6. A peptide in accordance with claim 3, wherein said peptide of a) is SEQ. ID NO.:15.

7. A peptide in accordance with claim 3, wherein the peptide of a) is SEQ. ID NO.:2.

8. A peptide in accordance with claim 3, wherein the peptide of a) is SEQ. ID NO.:4.

9. The peptide of claim 1 or 3, wherein said peptide of a) is SEQ. ID NO.:1.

10. The peptide of claim 1 or 3, wherein said peptide of a) is SEQ. ID NO.:3.

11. A composition comprising a peptide in accordance with claim 1 or 3 and a carrier.

12. The peptide of claim 1 or 3, wherein said peptide is a dimer.

13. The peptide of claim 1 or 3 wherein said peptide is a multimer.

14. The peptide of claim 13, wherein said peptide is a trimer.

15. The peptide of claim 1 or 3, wherein said peptide is conformationally constrained.

16. The peptide of claim 15, wherein said peptide is cyclized.

17. The peptide of claim 1 or 3, wherein said peptide has an N-terminal lauryl-cysteine (LC) and/or a C-terminal cysteine.

18. The peptide of claim 1 or 3, wherein said peptide has an N-terminal and C-terminal cysteine.

19. The peptide of claim 18, wherein said peptide has an intramolecular disulfide bridge.

20. The peptide of claim 1 or 3 wherein said peptide has an N-terminal and a C-terminal D-amino acid residue.

21. The peptide of claim 20, wherein the D-amino acid is D-alanine.

22. The peptide of claim 1 or 3, wherein said peptide has an N-terminal acetyl group.

23. The peptide of claim 1 or 3, wherein said peptide has a C-terminal D-amino acid residue.

24. The peptide of claim 23, wherein the D-amino acid is D-alanine.

25. An isolated peptide consisting of the amino acid sequence of SEQ. ID NO.:1 wherein said peptide does not have toxin agonist activity and is capable of antagonizing toxin-mediated activation of T-lymphocytes.

26. An isolated peptide consisting of the amino acid sequence of SEQ. ID NO.:2 wherein said peptide does not have toxin agonist activity and is capable of antagonizing toxin-mediated activation of T-lymphocytes.

27. An isolated peptide consisting of the amino acid sequence of SEQ. ID NO.:3 wherein said peptide does not have toxin agonist activity and is capable of antagonizing toxin-mediated activation of T-lymphocytes.

28. An isolated peptide consisting of the amino acid sequence of SEQ. ID NO.:4, wherein said peptide does not have toxin agonist activity and is capable of antagonizing toxin-mediated activation of T-lymphocytes.

29. An isolated peptide consisting of the amino acid sequence of SEQ. ID NO.:5 wherein said peptide does not have toxin agonist activity and is capable of antagonizing toxin-mediated activation of T-lymphocytes.

30. An isolated peptide consisting of the amino acid sequence of SEQ. ID NO.:6 wherein said peptide does not have toxin agonist activity and is capable of antagonizing toxin-mediated activation of T-lymphocytes.

31. An isolated peptide consisting of the amino acid sequence of SEQ. ID NO.:7 wherein said peptide does not have toxin agonist activity and is capable of antagonizing toxin-mediated activation of T-lymphocytes.

32. An isolated peptide consisting of the amino acid sequence of SEQ. ID NO.:8 wherein said peptide does not have toxin agonist activity and is capable of antagonizing toxin-mediated activation of T-lymphocytes.

33. An isolated peptide consisting of the amino acid sequence of SEQ. ID NO.:9 wherein said peptide does not have toxin agonist activity and is capable of antagonizing toxin-mediated activation of T-lymphocytes.

34. An isolated peptide consisting of the amino acid sequence of SEQ. ID NO.:10 wherein said peptide does not have toxin agonist activity and is capable of antagonizing toxin-mediated activation of T-lymphocytes.

35. An isolated peptide consisting of the amino acid sequence of SEQ. ID NO.:11 wherein said peptide does not have toxin agonist activity and is capable of antagonizing toxin-mediated activation of T-lymphocytes.

36. A composition which inhibits pyrogenic exotoxin-mediated activation of T-lymphocytes comprising an isolate comprising an isolated and purified peptide in accordance with claim 1 in an amount effective to inhibit exotoxin-induced expression of an RNA encoded by the IL-2, IFN-γ, and/or TNF-β genes, and a carrier.

37. The composition of claim 36, wherein the peptide has a sequence selected from the group consisting of SEQ. ID NO.:1, SEQ. ID NO.:2, SEQ. ID NO.:3, SEQ. ID NO.:4, SEQ. ID NO.:5, SEQ. ID NO.:6, SEQ. ID NO.:7, SEQ. ID NO.:8, SEQ. ID NO.:9, SEQ. ID NO.:10, and SEQ. ID NO.:11.

38. The composition of claim 36, wherein the peptide has a sequence selected from the group consisting of SEQ. ID NO.:2, SEQ. ID NO.:6, SEQ. ID NO.:7, SEQ. ID NO.:8, SEQ. ID NO.:9, SEQ. ID NO.:10 and SEQ. ID NO.:11.

39. The composition of claim 36, wherein the peptide has the sequence of SEQ. ID NO.:2.

40. An immunogenic composition for eliciting antibodies that block pyrogenic exotoxin mediated activation of T-lymphocytes comprising an isolated and purified peptide in accordance with claim 1 in an amount effective to elicit said antibodies, and a carrier.

41. The immunogenic composition of claim 40, further comprising an adjuvant selected from the group consisting of proteosomes, KLH, alum and mixtures thereof.

42. The immunogenic composition of claim 40, wherein the peptide has a sequence selected from the group consisting of SEQ. ID NO.:1, SEQ. ID NO.:2, SEQ. ID NO.:3, SEQ. ID NO.:4, SEQ. ID NO.:5, SEQ. ID NO.:6, SEQ. ID NO.: 7, SEQ. ID NO.:8, SEQ. ID NO.:9, SEQ. ID NO.:10 and SEQ. ID NO.:11.

43. The immunogenic composition of claim 40, wherein the peptide has a sequence selected from the group consisting of SEQ. ID NO.:2, SEQ. ID NO.:6, SEQ. ID NO.: 7, SEQ. ID NO.:8, SEQ. ID NO.:9, SEQ. ID NO.:10 and SEQ. ID NO.:11.

44. The immunogenic composition of claim 40, wherein the peptide has the sequence of SEQ. ID NO.:2.

45. An immunogenic composition for eliciting protective immunity against toxic shock comprising an isolated and purified peptidein accordance with claim 1 in an amount effective to elicit said protective immunity, and a carrier.

46. The peptide of claim 3, wherein the peptide is capable of eliciting antibodies that block pyrogenic exotoxin-mediated activation of T-lymphocytes.

47. The composition of claim 36, wherein, in said peptide, said peptide of a) consists of a dodecamer that is part of said domain consisting of amino acids 150–161, using the amino acid number of SEB.

48. The immunogenic composition of claim 40, wherein, in said peptide, said peptide of a) consists of a dodecamer that is part of said domain consisting of amino acids 150–161, using the amino acid number of SEB.

* * * * *